(12) United States Patent
Altrichter et al.

(10) Patent No.: US 10,377,987 B2
(45) Date of Patent: Aug. 13, 2019

(54) METHOD FOR PRODUCING A LEUKOCYTE PREPARATION

(71) Applicants: ARTCLINE GMBH, Rostock (DE); FRAUNHOFER-GESELLSCHAFT ZUR FÖRDERUNG DER ANGEWANDTEN FORSCHUNG E.V., München (DE)

(72) Inventors: Jens Altrichter, Kavelstorf (DE); Steffen Mitzner, Rostock (DE); Antje Lübcke, Schwerin (DE); Kathleen Selleng, Greifswald (DE); Fanny Doss, Rostock (DE); Stephanie Koch, Rostock (DE)

(73) Assignees: Artcline GmbH, Rostock (DE); Fraunhofer-Gesellschaft Zur Forderung Der Angewandten Forschung E.V., Munich (DE)

( * ) Notice: Subject to any disclaimer, the term of this patent is extended or adjusted under 35 U.S.C. 154(b) by 175 days.

(21) Appl. No.: 14/563,474

(22) Filed: Dec. 8, 2014

(65) Prior Publication Data

US 2015/0218515 A1 Aug. 6, 2015

Related U.S. Application Data

(63) Continuation of application No. PCT/EP2013/001664, filed on Jun. 6, 2013.

(30) Foreign Application Priority Data

Jun. 8, 2012 (DE) .................. 10 2012 209 673

(51) Int. Cl.
*A61K 35/16* (2015.01)
*C12N 5/0783* (2010.01)

(52) U.S. Cl.
CPC ............ *C12N 5/0636* (2013.01); *A61K 35/16* (2013.01)

(58) Field of Classification Search
None
See application file for complete search history.

(56) References Cited

U.S. PATENT DOCUMENTS

| | | | |
|---|---|---|---|
| 4,004,975 A * | 1/1977 | Lionetti | A01N 1/02 424/534 |
| 4,663,058 A * | 5/1987 | Wells | A61M 1/3695 210/519 |
| 4,765,899 A * | 8/1988 | Wells | B01D 21/02 210/519 |
| 2008/0053203 A1 | 3/2008 | Hogberg et al. | |

FOREIGN PATENT DOCUMENTS

| | | |
|---|---|---|
| DE | 3249215 C2 | 6/1990 |
| WO | 9510291 A1 | 4/1995 |
| WO | 2005032565 A1 | 4/2005 |
| WO | 2007131495 A2 | 11/2007 |

OTHER PUBLICATIONS

Bashir, et al., "Neutrophil function is preserved in a pooled granulocyte component prepared from whole blood donations", British Journal of Haematology, 2008, 140, pp. 701-711.
Altrichter, et al., "Extracorporeal cell therapy of septic shock patients with donor granulocytes: a pilot study", Critcal Care, http://ccforum.com/content/15/2/R82, 2011, pp. 1-13.
Ferrante, et al., "Optimal Conditions for Simultaneous Purification of Mononuclear and Polymorphonuclear Leucocytes From Human Blood by the Hypaque-Ficoll Method", Journal of Immunological Methods, 36, 1980, pp. 109-117.
Ferrante, et al., "A Rapid One-Step Procedure for Purification of Mononuclear and Polymorphonuclear Leukocytes from Human Blood Using a Modification of the Hypaque-Ficoll Technique", Journal of Immunological Methods, 24, 1978, pp. 389-393.
Meyer, et al., "Filter Biffy Coats (FBC): A source of peripheral blood leukocytes recovered from leukocyte depletion filters", Journal of Immunological Methods, 307, 2005, pp. 150-166.
Hubel,et al., "Effective storage of granulocytes collected by centrifugation leukaphersis from donors stimulated with granulocyte-colony-stimulating factor", 1878 Transfusion, 45, Dec. 2005, 14 pgs.
Mochizuki et al., "Extended storage of granulocyte concentrates mobilized by G-CSF with/without dexamethasone and collected by bag separation method," Transfusion Medicine 2007, 17 (4) pp. 296-303.
Querschnitts-Leitlinien (BÄK) zur Therapie mit Blutkomponenten und Plasmaderivaten, 4th edition, 2008, issued by Vorstand der Bundesärztekammer on the recommendation of the Wissenschaftlichen Beirats, pp. 157.
Schroeder M. L., "Transfusion-associated graft-versus-host-disease", Br J Haematol 117, (2002) pp. 275-287.

* cited by examiner

*Primary Examiner* — Blaine Lankford
(74) *Attorney, Agent, or Firm* — Murtha Cullina LLP

(57) ABSTRACT

A method for preparing a leukocyte preparation from a leukocyte fraction and a correspondingly prepared or obtainable leukocyte preparation and its use. The method includes: a) sedimenting the leukocyte fraction removing leukocyte supernatant from the sediment, wherein the leukocyte supernatant is collected or remains in a leukocyte container, b) sedimenting the leukocytes in the leukocyte container, c) washing the sediment in the leukocyte container with a saline solution, and d) resuspending the sediment in the leukocyte container in a storage solution.

17 Claims, 17 Drawing Sheets

METHOD FOR PRODUCING A LEUKOCYTE PREPARATION

CROSS REFERENCE TO RELATED APPLICATIONS

Figure 1:
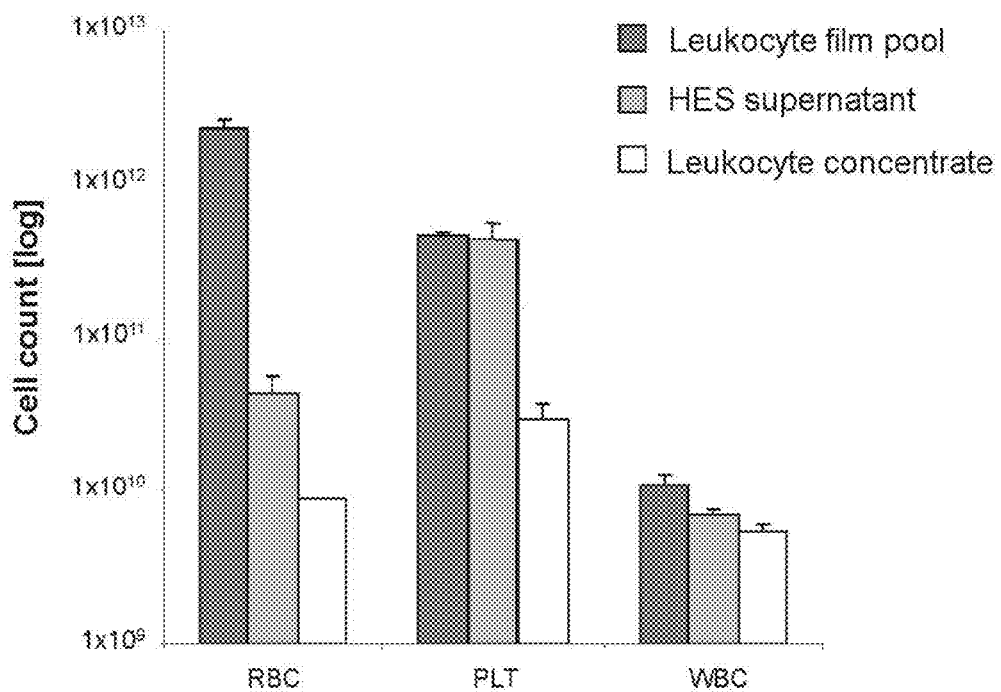

The present application is a continuation application and claims priority benefit under 35 USC § 120 to PCT Patent Application No. PCT/EP2013/001664, filed on Jun. 6, 2013, which PCT application claims priority benefit to German Patent Application No. 10 2012 209 673.6, filed on Jun. 8, 2012, the entireties of which are incorporated by reference herein.

The invention relates to a method for preparing a leukocyte preparation from a leukocyte fraction. The invention further relates to a correspondingly prepared or obtainable leukocyte preparation and its use.

The transfusion of leukocytes (white blood cells), more particularly granulocytes, is a supportive therapy in patients with life-threatening neutropenia or with neutrophil dysfunction. In said patients, granulocyte transfusions can also control or prevent infections. Said granulocyte transfusions consist of blood plasma containing enriched granuloyctes, a type of leukocyte, but also additionally contain very high numbers of thrombocytes (platelets) and erythrocytes (red blood cells). These applications require large amounts of granulocytes, typically from $1 \cdot 10^{10}$ to $8 \cdot 10^{10}$ granulocytes per apheresis.

To date, granulocyte apheresis products, also referred to as "granulocyte concentrates", are acquired from the blood of healthy donors. Generally, the donors are stimulated with steroids, for example glucocorticoids such as dexamethasone or prednisolone, and/or growth factors, for example the granulocyte colony-stimulating factor (G-CSF), 2 to 24 hours before donation. Donation is achieved by apheresis, in which blood is guided via a catheter into a piece of tubing, mixed therein with citrate and a sedimentation accelerator, and transferred to a centrifuge. In the centrifuge, the plasma and the erythrocytes are pumped off on the inside and on the outside, respectively, mixed, and reinfused into the patient under computer control. By means of suitable pump speeds for the plasma and erythrocytes, the leukocyte-containing intermediate layer is brought under a middle outlet opening and pumped from here into a bag. "Granulocyte apheresis products", which are highly impure, are acquired as a result.

The terms "granulocyte apheresis product" or "granulocyte concentrate" are deceptive, because what is actually concerned is rather a granulocyte-enriched whole blood. There are approximately 10-100-fold more erythrocytes and thrombocytes than leukocytes in the apheresis product. In the case of donors prestimulated with steroids and/or G-CSF, generally more than 50% of leukocytes are granulocytes.

Granulocyte apheresis product acquired in such a way is not storable and, depending on state law, must be used for clinical purposes within from 6 hours up to a maximum of 24 hours. The reason for this is that granulocytes in blood only have a short lifespan, with the mean blood residence time being approximately one day. Furthermore, granulocytes and monocytes are activated rapidly and very strongly by nonphysiological conditions, releasing oxygen radicals and enzymes which harm even the cells themselves ("kamikaze effect"). This short shelf life and the activation of cells prevent both a broader investigation in research and the use for treating infections.

In order to obtain appropriately large amounts of leukocytes, and more particularly granulocytes, donors are to date treated with glucocorticoids and/or so-called granulocyte colony-stimulating factor (G-CSF), stimulating the production of granulocytes, and after the granulocyte amount in the donor blood has risen, an apheresis of the peripheral blood is carried out in order to collect these cells. The stimulation of the donor by G-CSF may be associated with negative effects for the donor such as pain or fever.

An alternative option, which optionally manages without stimulation of the donor, is the preparation of a leukocyte preparation from leukocyte films (buffy coats, or BCs for short) from whole blood without apheresis. To this end, the donated whole blood samples of approximately 450 ml to 500 ml are typically fractionated into an erythrocyte concentrate and into plasma after sedimentation or centrifugation. Remaining in the residual bag, from which the erythrocyte concentrate and the plasma have been removed, is the leukocyte film, which formed between the two fractions and which contains the predominant portion of leukocytes and thrombocytes of the donor. Erythrocytes are depleted in the leukocyte film and still dominate the leukocyte film.

In some cases, the leukocyte films from two or more donated whole blood samples are pooled in order to form thrombocyte concentrates. In this case, most of the leukocyte films and more particularly the leukocytes are treated as waste.

The use of leukocyte preparations is known per se. Leukocytes are built up from various leukocyte types having different properties, including granulocytes, lymphocytes and monocytes.

Shelf life is especially important for clinical usability and for usability in clinical research. Some frequently occurring leukocyte types such as the granulocytes are only very briefly storable or not storable at all and, in known leukocyte preparations, already lose their viability and functionality after a few hours, and so they must be typically stored and used for not longer than 24 hours. In addition, the leukocyte or granulocyte preparations typically used are highly contaminated with erythrocytes and thrombocytes. Because of the low shelf life, such preparations must be prepared and used directly after blood donation or apheresis. This is done on request.

In Bashir et al., Br. J. Haematol. 2008, 140 (6) 701-11, a granulocyte preparation was prepared from leukocyte films. To this end, leukocyte films were pooled, mixed with 400 ml of thrombocyte additive solution, and centrifuged. The resulting granulocyte-enriched layer was, with the addition of 70 ml of plasma, transferred to a thrombocyte collection bag. The corresponding product contained on average $8.8 \cdot 10^9$ neutrophils (granulocytes). The thrombocyte concentration was not substantially reduced. The granulocyte preparation was stored under constant conditions for 68 hours. After 68 hours, the survival rate was 84%, and phagocytosis and respiratory burst had dropped to 94% and 81% in comparison with the time immediately after preparation. There was a very high contamination with erythrocytes and thrombocytes.

In Mochizuki et al., Transfus. Med. 2007, 17 (4), 296 to 303, the influence of donor pretreatment on granulocyte function after 72 hours was investigated using a bag separation method. An untreated control, which corresponded to a leukocyte film, was used as comparison. During storage at room temperature, a 10% loss of granulocytes was found. The survival rate (viability) was 96%. Respiratory burst and phagocytosis proportions at the start remained comparatively stable, though phagocytosis dropped to 83% in relation to the start. Here too, there was a very high contamination with erythrocytes and thrombocytes.

In contrast, it is an object of the present invention to specify a method for preparing a leukocyte preparation, more particularly a granulocyte preparation, and also a corresponding leukocyte preparation storable beyond 24 hours without substantial loss of viability and functionality of the leukocytes and more particularly granulocytes contained therein, the intention being to deplete the erythrocytes and thrombocytes with respect to the leukocytes more strongly than is possible to date.

This object is achieved by method for preparing a leukocyte preparation from a leukocyte fraction, comprising the following method steps:

a) sedimenting the leukocyte fraction until a dividing line has formed between the sedimented erythrocytes and a leukocyte supernatant, removing the leukocyte supernatant from the sediment, wherein the leukocyte supernatant is collected or remains in a leukocyte container, b) sedimenting the leukocytes in the leukocyte container, wherein a low-leukocyte supernatant is formed, and removing the low-leukocyte supernatant from the leukocyte container, c) washing the sediment in the leukocyte container with a saline solution, wherein the sedimented cells are resuspended in the saline solution, the solution is sedimented and a resulting supernatant is removed, and d) resuspending the sediment in the leukocyte container in a storage solution.

For the purposes of this application, the term leukocyte fraction encompasses those leukocyte-containing cell mixtures acquired as leukocyte apheresis product, as well as leukocyte film acquired from whole blood and other cells treated in cell culture, for example bone marrow punctate, stem cell apheresis product, but also whole blood itself and cord blood.

This method according to the invention can be used both in the case of leukocyte apheresis products from donated whole blood samples from stimulated donors and from leukocyte films from donated whole blood samples from nonstimulated or stimulated donors and is based on a combination of sedimentation and washing steps. The leukocyte fraction as starting material typically contains anticoagulants, for example citrate-phosphate-dextrose (CPD) or acid-citrate-dextrose (ACD). The methods for preparing the leukocyte fraction as leukocyte apheresis product or from leukocyte film is known per se, the latter for example by centrifuging a donated whole blood sample at high acceleration, for example acceleration of 4000 g for 10 min at room temperature.

In the context of the invention, the term "leukocytes" in conjunction with "leukocyte fraction", "leukocyte preparation" or the like also encompasses granulocytes, granulocyte fractions and granulocyte preparations and also fractions of other leukocytes which are not granulocytes.

The method according to the invention makes it possible to acquire leukocyte fractions in which, compared to whole blood, more than 90%, more particularly more than 98%, of the erythrocytes and more than 90% of the thrombocytes are removed and the cells are storable for at least 72 hours without substantial loss of function.

Preferably, the solution in the leukocyte container after method step d) is stored in a method step e), more particularly at a temperature from −200° C. to +40° C., more particularly at +2° C. to +38° C., more particularly at +20° C. to +25° C., or frozen and stored at −50° C. to −200° C. in a cryopreservation procedure. This makes it possible, even after a prolonged storage period, for example up to 168 hours or more, to provide leukocyte preparations which still function.

Cryopreservation during storage is also advantageous, with freezing and storage at −50° C. to −200° C., for example in liquid nitrogen or in a gas phase above liquid nitrogen.

Preferably, sedimentation is carried out in method step a) at an acceleration from 0.5 g to 1000 g, more particularly from 0.5 g to 1.5 g or from 50 g to 1000 g, and/or with the addition of a sedimentation accelerator, more particularly hydroxyethyl starch, dextran, Ficoll, Percoll and/or gelatin, wherein the sedimentation time in particular is between 5 and 120 minutes, preferably between 20 and 45 minutes. Sedimentation of the leukocyte fraction is thus carried out at low acceleration, for example at an acceleration of 1 g, i.e. gravitational acceleration (gravitation), or is supported by centrifugation. In this connection, adding a sedimentation accelerator may help. The ratio of cell mixture to sedimentation accelerator is preferably 1:0.2 to 1:20, preferably 1:0.4 to 1:2. After a few minutes, a sediment containing erythrocytes is separated from a low-erythrocyte supernatant. The supernatant is enriched with leukocytes. Depending on the method of sedimentation, either the leukocyte supernatant is filled into a leukocyte container, for example a bag, and thus separated from the sediment or the sediment is discharged from the leukocyte container in which sedimentation took place and discarded.

Sedimentation of the leukocytes in method step b) and/or sedimentation in method step c) is preferably carried out by centrifugation, more particularly at an acceleration from 50 to 10 000 g, more particularly at 100 to 5500 g, more particularly at 200 to 500 g. This makes it possible to effectively separate the leukocytes from the thrombocytes.

Sedimentation is preferably carried out in a flexible bag. After adding a sedimentation accelerator and prior to sedimentation, the air present should advantageously be pressed out of the bag and reentry of air prevented by closure of the outlet (e.g. by means of a clamp). During sedimentation, the bag should preferably not be moved. For the purposes of air displacement and motionless storage, a device into which the bag is suspended is advantageously used. The sediment can be displaced from a lower outlet by pressure difference or gravity; the supernatant can be displaced from an upper outlet by pressure difference. Removal of the sediment by gravity can be controlled by a clamp or a pump. Generating a pressure difference in order to displace the sediment to the bottom or the supernatant to the top can be supported by a suction pump (negative pressure) or by generating a positive pressure around the sedimentation bag. The pressure difference can be generated manually, for example by a manual blood bag press, or by machine. For example, the sedimentation bag can be advantageously accommodated within a further bag or a pressure-tight chamber, in which a positive pressure can be generated by introducing a gas or a liquid. Alternatively, it is likewise advantageously possible to generate a negative pressure in the removal tubing, for example by means of a (peristaltic) pump. The end of separation is determined by each different component reaching the bag outlet and is generally associated with a change in color and/or optical density of the content. This result can be identified visually by the operator, in an automated system, but also by a, for example, optical detector.

The wash in method step c) is preferably repeated one or more times. Repeating the wash serves to further clean up the leukocyte preparation and deplete thrombocytes and possibly erythrocytes.

The wash or washes in method step c) is or are preferably carried out by means of centrifugation and/or filtration. Further advantageously, the wash or washes in method step c) is or are carried out with a physiological solution containing in particular 50 to 200 mM sodium chloride and/or further salts and/or buffers.

For the purposes of transferring liquids from one bag to another during the wash procedures and addition of additives, it is advantageously possible to use the same manual or automated technique or to use gravity as described above for separating sediment and supernatant.

Method step e) involving storage is preferably carried out in a gas-permeable bag. This allows carbon dioxide which forms in the storage solution to escape or vent, and so the pH of the solution drops less rapidly than in the case of a gas-impermeable bag in which carbon dioxide forms, acidifying the storage solution. The possible storage period is prolonged as a result.

Preferably, the storage solution is a blood group-identical blood plasma and/or an aqueous solution containing in particular blood group-identical plasma.

The method according to the invention is preferably carried out at room temperature, more particularly preferably at 22±2° C.

Preferably, the method is carried out aseptically in a closed system, more particularly in a system of tubing and bags. Appropriate measures for aseptically connecting tubing and bags to one another and separating them are known and are used as standard. For this purpose, appropriate known sterile tubing welds are used for example. Alternatively, tubing connections can be advantageously established by aseptic techniques, for example by sterile Luer connections or suitable sterile cannulae or needles in connectors or puncturable septa, as used in infusion systems.

Before, during or after any of method steps a) to d), additives are preferably added, more particularly from the groups of the pH-stabilizing substances, more particularly buffer, of the nutrients, more particularly glucose, of the function improvers, more particularly cytokines and/or growth factors, of the blood plasma components, more particularly blood group-identical blood plasma and/or albumin, and/or of the antioxidants, more particularly ascorbic acid, glutathione, cysteine, or methionine, in order to improve storage. The additives can also still be added during storage.

For example, a preferred additive solution is PAGGS-M, which contains not only sodium chloride, sodium dihydrogen phosphate dihydrate and disodium hydrogen phosphate dihydrate, but also glucose monohydrate, mannitol, adenine and guanosine. This additive is preferably to be used during storage. A further advantageously usable additive, which is preferably used during storage, is the immune system-related preparation Immuno-akut®, which contains not only vitamins B6, B12, C, D and E, but also folic acid, various carotenoids and trace elements. The individual stated constituents of PAGGS-M and/or Immuno-akut® can also be added individually as additive.

Before, during and/or after any of method steps a) to d), multiple preparations are advantageously pooled. This leads to a release of cytokines by the leukocytes, which improve shelf life as a result of their positive effect on the lifespan of the granulocytes.

The effect of the so-called "mixed leukocyte reaction" (also known as "mixed lymphocyte reaction", or MLR for short) is hereby used for the first time for prolonging storage of granulocytes. In the MLR, two populations of allogeneic lymphocytes (lymphocytes from genetically different individuals of the same species) are mixed, resulting primarily in a T-cell activation, mediator release and possibly proliferation. In this connection, the cell surface antigens of the major histocompatibility complex (MHC) are probably the greatest stimuli.

In a pooled leukocyte preparation, the released mediators, especially cytokines and growth factors, also activate the other leukocytes, for example granulocytes, and improve their shelf life and activity. Alternatively or additionally, multiple leukocyte preparations can also be pooled only after storage in the last few hours or even minutes before use, in order to use the mediator release immediately for stimulating the leukocytes in the leukocyte preparation or in the patient.

Use of a pooled leukocyte preparation can also consist in transferring the virtually or completely cell-free, though mediator-containing, supernatant of the leukocyte preparation to a separate container and infusing it into a patient for immunostimulation. In this connection, transfer techniques mentioned elsewhere can be used.

Before or after at least one of method steps a) to e) or immediately before use, an irradiation, more particularly with γ-rays, advantageously takes place, more particularly with a dose of at least 25 Gy, more particularly at least 30 Gy. According to the Querschnitts-Leitlinien (BÄK) zur Therapie mit Blutkomponenten and Plasmaderivaten [Cross-Sectional Guidelines (German Medical Association) for Therapy with Blood Components and Plasma Derivatives], 4th edition 2008, published by the Executive Committe of the German Medical Assocation on the recommendation of the Scientific Advisory Board, page 157, and Schroeder M. L., "Transfusion-associated graft-versus-host disease", Br J Haematol 117, 275-287 (2002), irradiation with a mean dose of 30 Gy (at no part of the product less than 25 Gy) brings about a reliable inhibition of T-cell proliferation, whereas the function of erythrocytes, thrombocytes and granulocytes after irradiation remains largely unimpaired.

The object underlying the invention is also achieved by a leukocyte preparation prepared or obtainable in an above-described method according to the invention. The leukocyte preparation is preferably distinguished by the fact that, with respect to whole blood, the erythrocytes are reduced by more than 90%, more particularly more than 98%, and the thrombocytes by more than 90%, whereas the leukocytes are reduced by not more than 60%. Furthermore, it is storable preferably at a temperature between 2° C. and 38° C. for a period of more than 24 hours to 168 hours without substantial loss of function, wherein in particular respiratory burst and/or phagocytosis is or are still, even after 72 hours of storage, more than 90% of the corresponding values of the fresh leukocyte preparation.

Since the leukocyte preparation is prepared or obtainable in accordance with the method according to the invention, it has the corresponding advantages, properties and features as described above.

Furthermore, the object underlying the invention is also achieved by use of an above-described, more particularly pooled, leukocyte preparation according to the invention for preparing a substantially cell-free supernatant having a high mediator concentration and/or in an extracorporeal circulation or for infusion. With the last-mentioned alternatives, clinical research or clinical treatments with leukocyte or granulocyte preparations are possible without prior request, since the preparations are available when needed without having to be specifically freshly prepared. The use of a granulocyte preparation according to the invention in an extracorporeal circulation is, for example, possible in a method as described in Altrichter et al., Critical Care, 2001, 15:R82 "Extracorporeal cell therapy of septic shock patients with donor granulocytes: a pilot study".

The use of a pooled leukocyte preparation for preparing a substantially cell-free supernatant having a high mediator concentration and to be transferred to a separate container has the advantage that the supernatant can be infused into a patient for immunostimulation. In this connection, above-mentioned transfer techniques can be used.

Likewise advantageous is use of the cell-free liquid portions of a leukocyte preparation according to the invention for infusion as immunostimulant.

The object underlying the invention is also achieved by a preparation system which is composed of bags and tubing and which is designed and set up for carrying out an above-described method according to the invention for preparing a leukocyte preparation, and also by a preparation device which for the automated or semiautomated performance of the above-described method according to the invention for preparing an above-described leukocyte preparation according to the invention, more particularly using an above-described preparation system according to the invention.

Further features of the invention are evident from the description of embodiments according to the invention together with the claims and the attached drawings. Embodiments according to the invention may satisfy individual features or a combination of multiple features.

Figure 2:
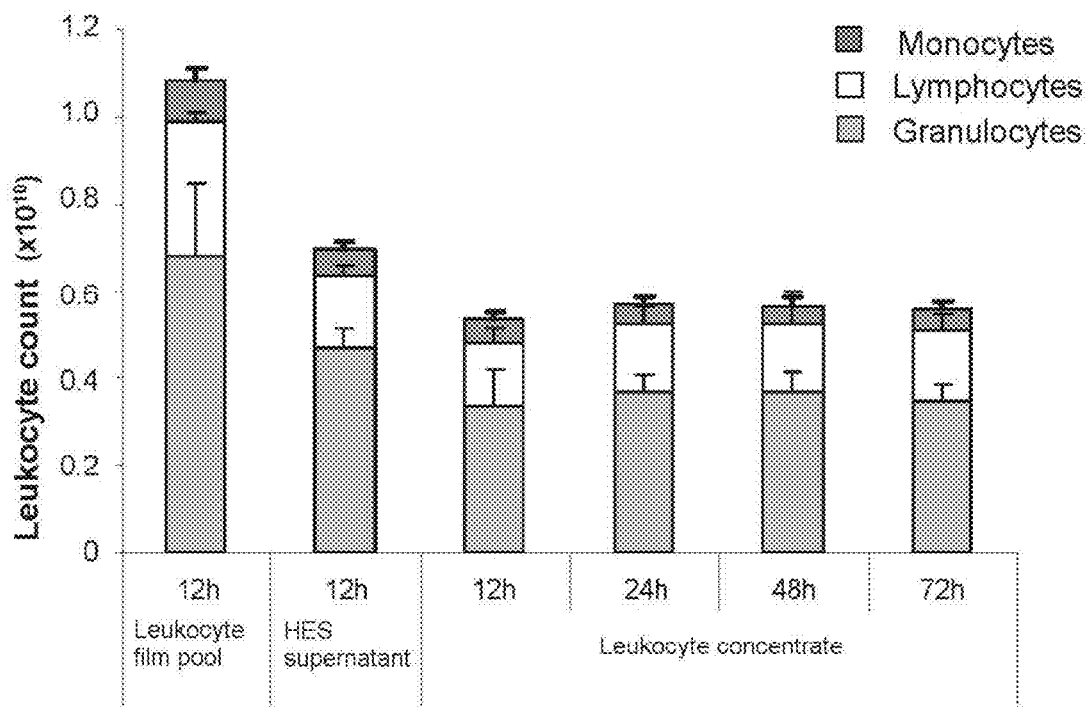
Figure 3:
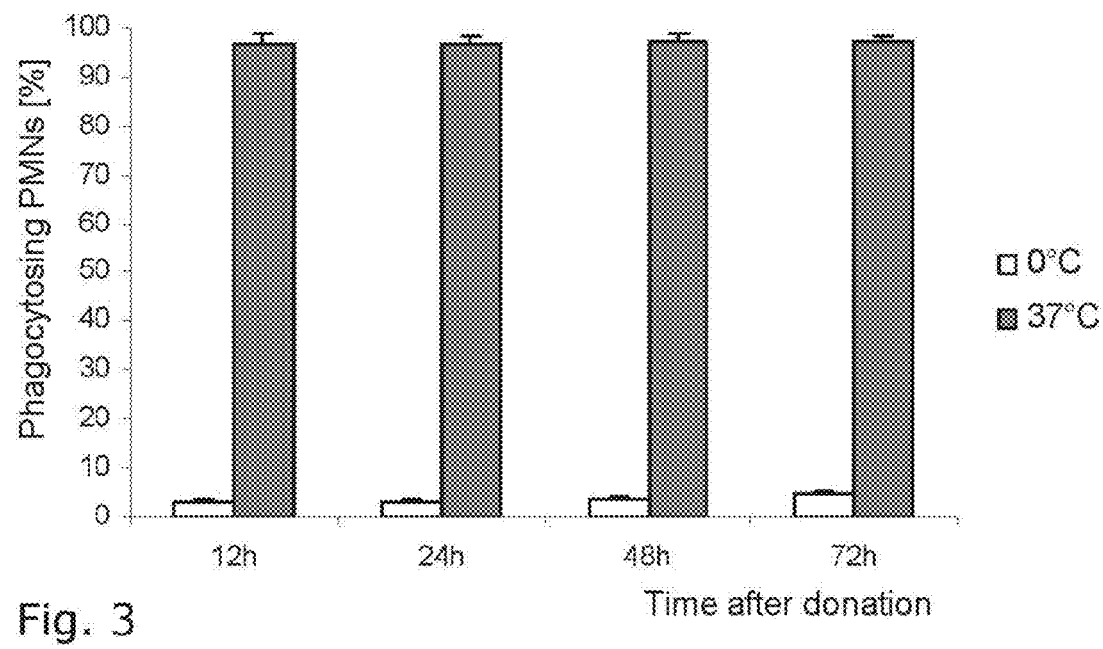
Figure 4:
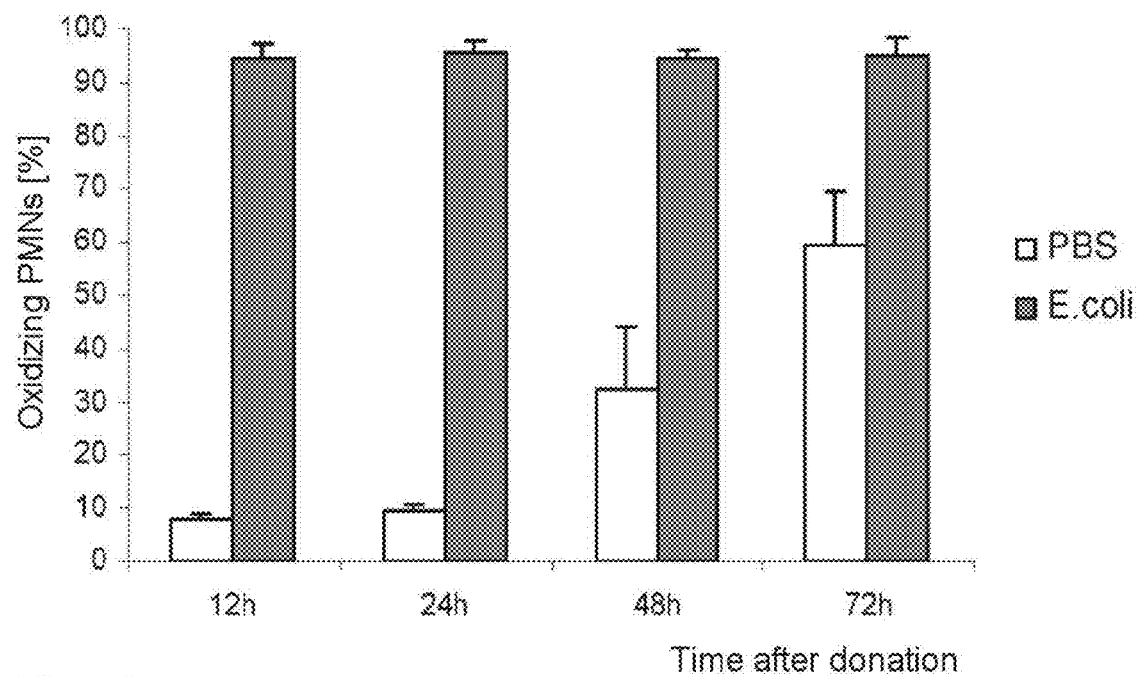
Figure 5:
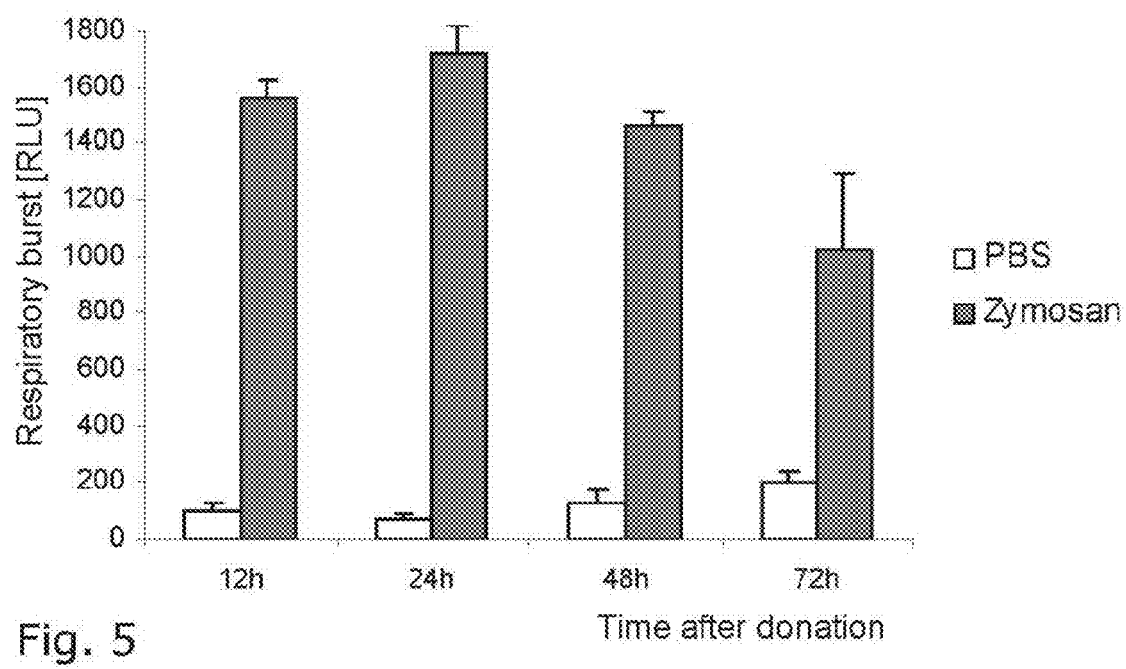
Figure 6:
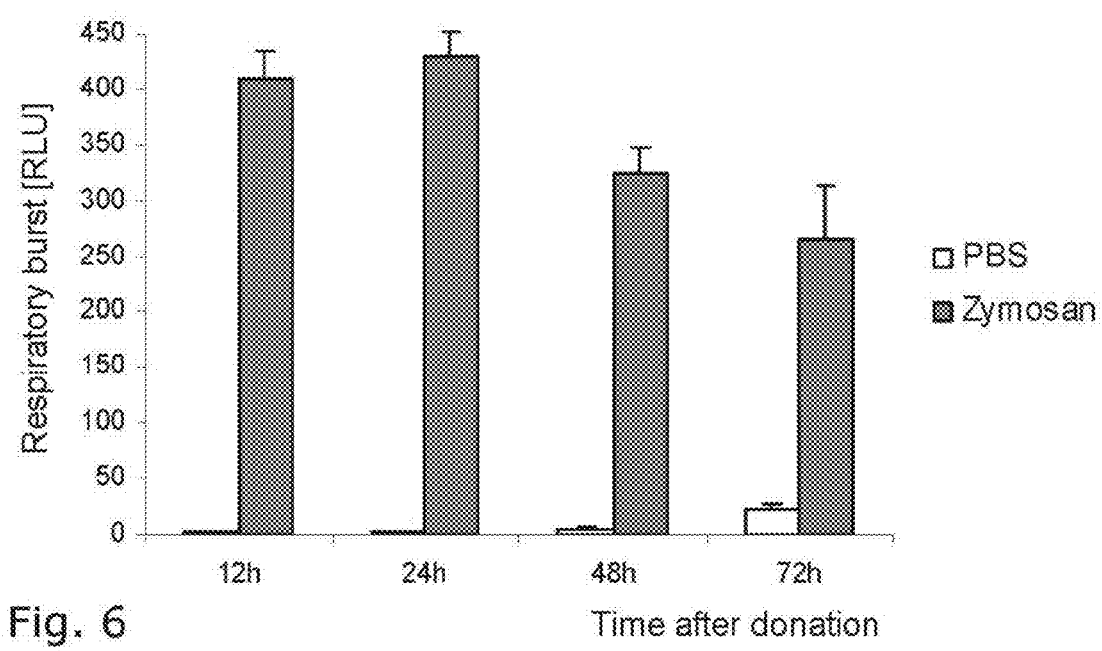
Figure 12:
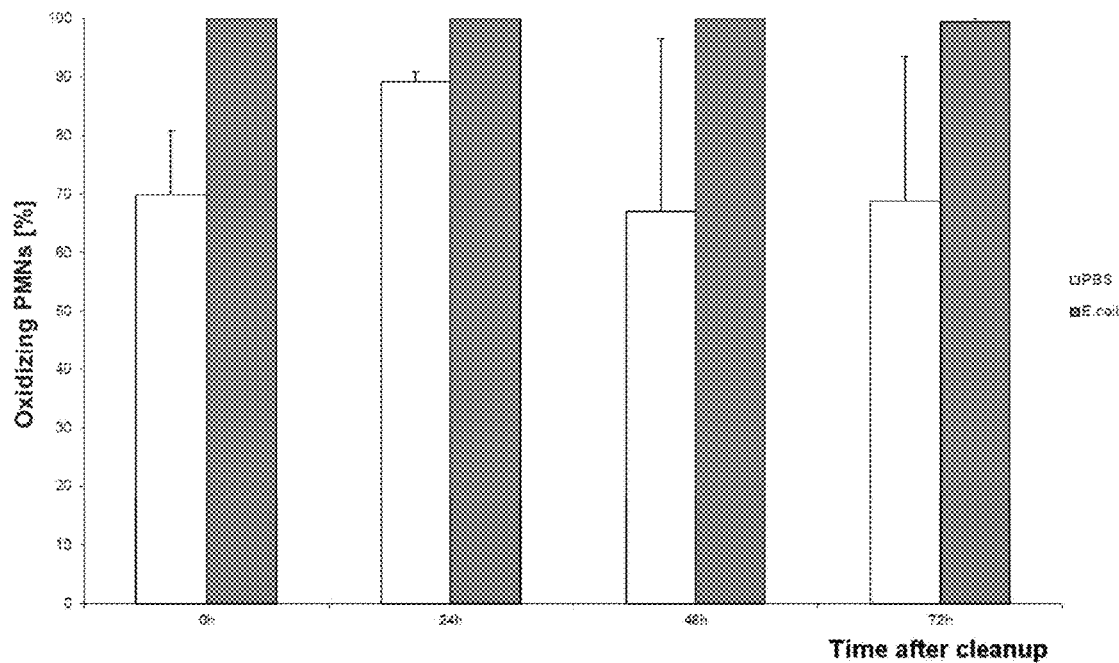
Figure 13:
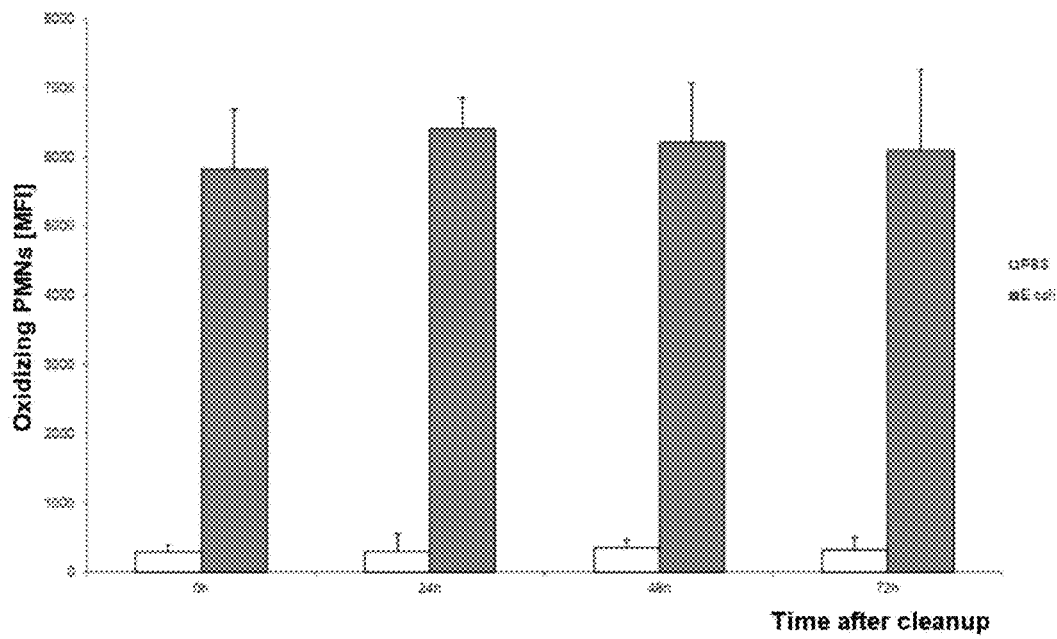
Figure 31:
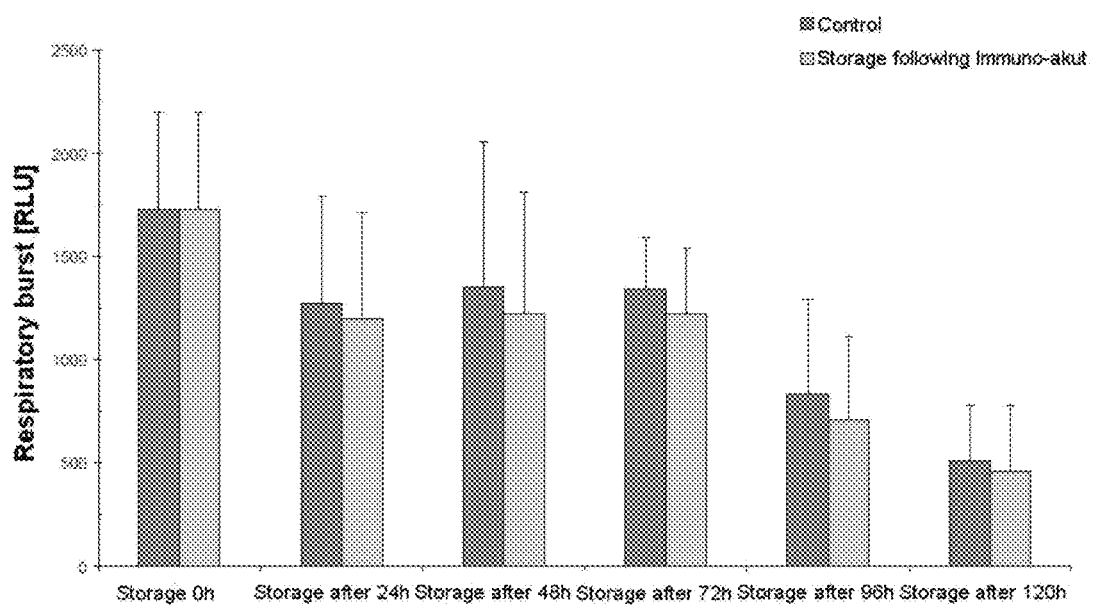
Figure 14:
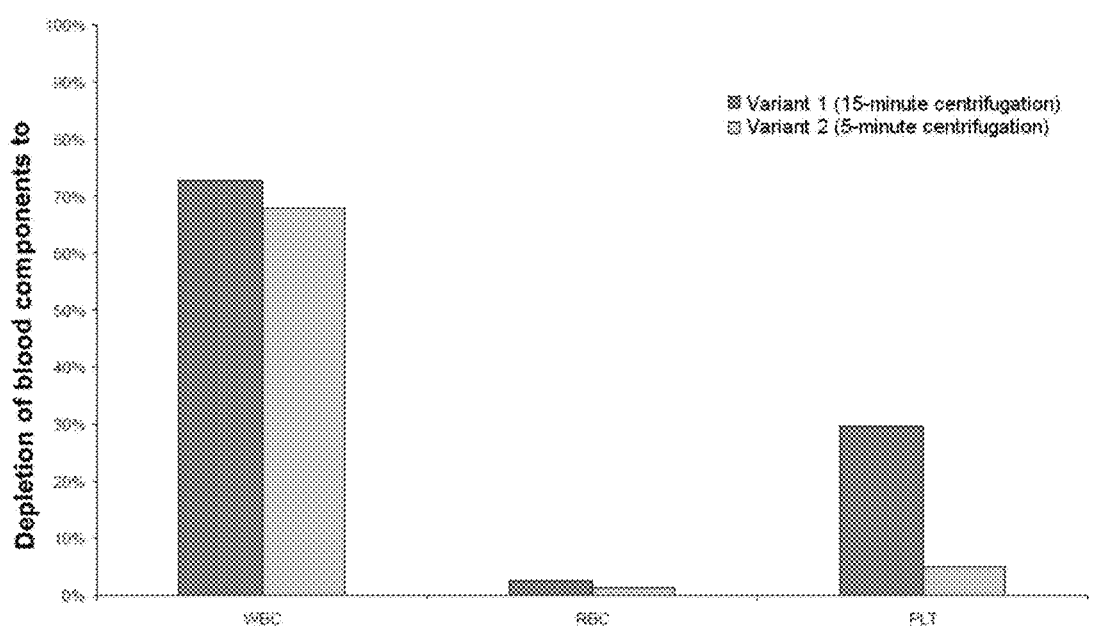
Figure 32:
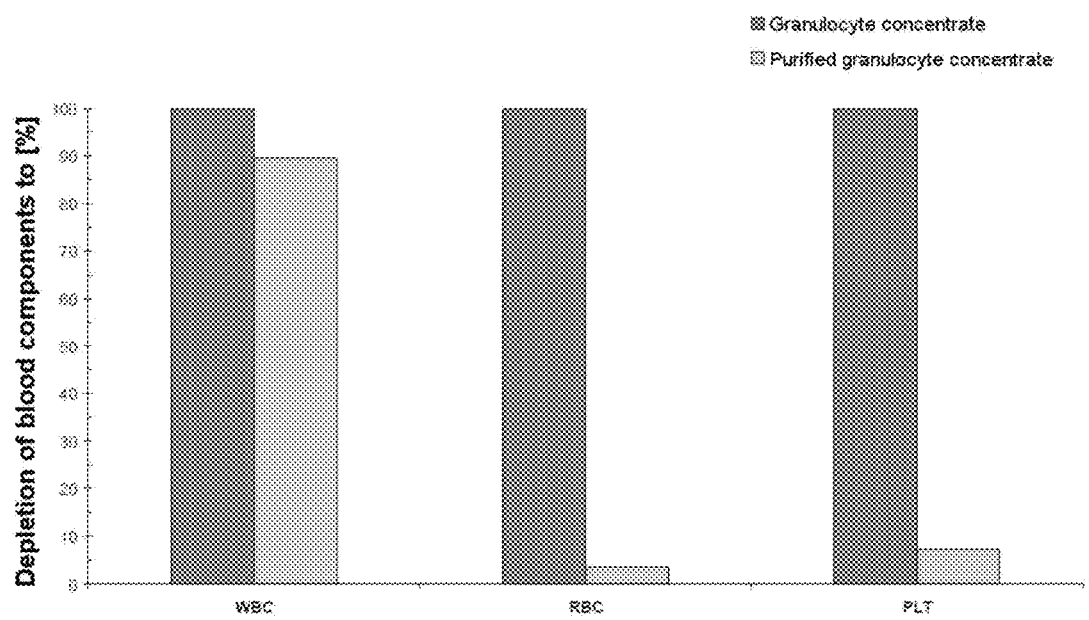
Figure 33:
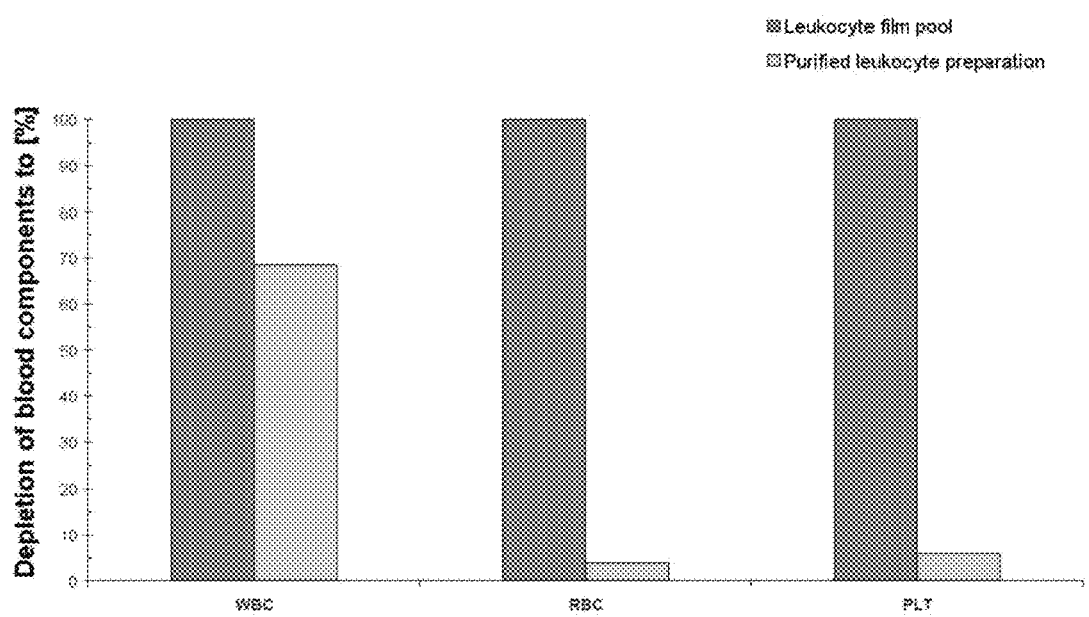

The invention will be described below on the basis of exemplary embodiments with reference to the figures without restricting the general concept of the invention, and with regard to all details according to the invention that are not explained in more detail in the text, reference is expressly made to the drawings. What is shown are:

FIG. 1 the counts for different cell types in different method steps of the method according to the invention, FIG. 2 the cell type counts during storage of a granulocyte preparation according to the invention, FIG. 3 the progression of phagocytosis over time during storage, FIGS. 4 to 6 the progression of respiratory burst over time for a granulocyte preparation according to the invention under different conditions and measurement methods during storage and FIGS. 7 to 13 results of a second exemplary embodiment according to the invention, FIG. 14 results of a third exemplary embodiment according to the invention, FIGS. 15 to 18 results of a fourth exemplary embodiment according to the invention, FIGS. 19 to 24 results of a fifth exemplary embodiment according to the invention, FIGS. 25 to 31 results of a sixth exemplary embodiment according to the invention, FIGS. 32 to 33 results of a seventh exemplary embodiment according to the invention.

First Exemplary Embodiment

The preparation according to the invention of a leukocyte preparation or granulocyte preparation from leukocyte films (buffy coats) will be described below using a first example.

Preparing the Leukocyte Fraction

Firstly, donated whole blood samples between 450 ml to 500 ml containing CPD were centrifuged at 4000 g at 22° C. for 10 min. Plasma, leukocyte film and erythrocytes were separated within four hours after donation by a plasma expressor (MacoPharma, Langen, Germany).

For the preparation of a leukocyte concentrate, the leukocyte films from different donors were brought together (pooled). All bag and tubing connections were carried out using aseptic technique in accordance with industry standard.

Six leukocyte films between 62 ml and 82 ml from blood group-identical donors were joined together in series, i.e. the corresponding bags were connected to one another in series. The bags were gently massaged in order to detach the leukocytes adhering to the bag interior. The extensively mixed content of these leukocyte layers was collected altogether in the last bag of the series (pool bag). The clamps between the bags of the series were closed in order to prevent reflux.

500 ml of hydroxyethyl starch (HES for short, Infukoll HES 6% 200/0.5 KS (saline solution); Serumwerk, Bernburg, Germany) were filled into a transfer bag. The transfer bag was welded onto the first empty bag of the series under stable conditions and 50 ml of the HES solution were transferred into this bag, which was rinsed extensively therewith by swinging and manual massaging.

This method step was repeated with the following leukocyte layer bags, by opening each tubing passage and filling the next bag with 50 ml of HES/cells suspension. The connection was closed again in order to prevent reflux. Finally, the HES solution was filled into the pool bag. This "washing out of the leukocyte film bags" was carried out a second time.

Subsequently, the pool bag was separated from the leukocyte film bag series and directly connected to the HES bag or transfer bag. The pool bag was completely filled with HES solution and all air bubbles were removed. In this way, 416±13 ml of leukocyte film were mixed in the pool bag with about 258±30 ml of HES solution. In this way, the leukocyte fraction was prepared.

Preparing the Leukocyte Preparation

In order to prepare the leukocyte preparation from the leukocyte fraction, the pool bag was firstly connected to a transfer bag, with the connection continuing to remain closed. This unit was allowed to hang at 22±2° with the connection tubing hanging above and for 35 minutes without interference, and so the erythrocytes sedimented by gravity and a sharp dividing line formed between the sedimented erythrocytes and the leukocyte-enriched supernatant.

The pool bag was inserted into a plasma expressor (Mediros, Rostock, Germany) in order to transfer the enriched supernatant into the empty transfer bag ("leuko-bag") after the tubing connection was opened. The erythrocyte sediment was discarded (cf. method step a) of the method according to the invention).

The leuko-bag was connected to an empty bag, for example a washed-out leukocyte film bag from the bag series, with the connection continuing to remain closed. The bags were then centrifuged at 200 g at 22±2° C. for 7 min, forming a sediment of leukocytes and a plasma/HES solution supernatant containing most of the thrombocytes. Using the plasma expressor, this supernatant was transferred to the empty bag, which was removed and discarded (cf. method step b) of the method according to the invention).

Subsequently, two washes were carried out in order to further reduce the number of thrombocytes still present in the leukocyte sediment. To this end, the leuko-bag was connected to a bag containing 0.9% saline solution and about 30 ml of saline solution were transferred to the leuko-bag in order to resuspend the cell sediment by careful stroking by hand across the bag, before the leuko-bag was topped up with the saline solution to a total weight of 350 g.

Subsequently, the bag was centrifuged at 200 g, 22±2° C., for 7 min, the wash solution was pressed into an empty bag, and this bag was discarded (cf. method step c) of the method according to the invention). This wash procedure was repeated once.

Lastly, the leukocytes were resuspended in 200 ml of blood group-identical donor plasma from one of the leukocyte film donors in order to obtain the leukocyte preparation (method step d).

Storing the Leukocyte Preparation

The resulting leukocyte concentrate or the leukocyte preparation was transferred to a gas-permeable thrombocyte storage bag and gas bubbles were removed. The leukocyte concentrates were stored at room temperature without agitation, with the bags resting on grill grates in order to guarantee full contact of the bag surface with the air.

In the further exemplary embodiments, storage was also carried out in each case in gas-permeable thrombocyte storage bags.

Analysis

After 24, 48 and 72 hours, the leukocyte preparations were mixed in each case and, after the first milliliter was discarded, i.e. the content of the tubing end, 2 ml samples were collected in each case for analysis.

The concentrations of erythrocytes, thrombocytes and leukocytes were measured by automated counting (Sysmex KX-21N, Sysmex Corporation, Norderstedt, Germany). Blood smears were prepared in order to manually differentiate the leukocyte populations, more particularly monocytes, lymphocytes and granulocytes.

The shelf life of the leukocytes was established by a Trypan blue exclusion assay.

For the functional analysis by means of chemiluminescent analysis and flow cytometry, the leukocyte concentrations were modified by addition of corresponding blood plasma to $5 \cdot 10^6$ leukocytes per ml.

The production of oxygen radicals was investigated by means of chemiluminescence. To this end, the leukocytes were stimulated with serum-opsonized zymosan particles (Sigma-Aldrich, Deisenhofen, Germany) in order to determine respiratory burst (also known as "oxidative burst" or "oxyburst"). For the negative control, phosphate-buffered saline solution (PBS) was added. Chemiluminescence was amplified by lucigenin and luminol (Sigma-Aldrich, Deisenhofen, Germany) in two different assays.

For the chemiluminescence analysis, the samples were each filled three times into 96-well titer plates and luminescence was measured by an automatated chemiluminescence measurement instrument (RS Luminoskan Ascent, Thermo Fisher Scientific, Dreieich, Germany) directly after zymosan had been added. For 60 minutes, chemiluminescence was determined in individual relative light units (RLU) every 2 minutes. After completion of the measurements, the arithmetic mean of the triplicate measurements was calculated and the area under the curve (AUC) was determined by adding up said means.

For the measurement of functionality, phagocytosis and respiratory burst were additionally determined in fluorescence cytometry. For this purpose, heparin was added to the leukocyte preparation in a concentration of 25 international units (IU) per ml. Phagocytosis was determined by using the assay kit Phagotest®, and respiratory burst was analyzed by using the assay kit Phagoburst® (both from Orpegen, Heidelberg, Germany). The principle behind determining phagocytosis was based on incubating the cells with opsonized inactivated fluorescein-labeled (FITC-labeled) *E. coli* at a temperature of 37° C. for 20 minutes. Negative control samples were stored at 4° C.

Respiratory burst was assayed by incubating the cells with opsonized *E. coli*. The resulting formation of reactive oxygen species was determined by the amount of fluorescent rhodamine 20 minutes after incubation with dihydrorhodamine 123 (DHR 123) at 37° C. A sample with no addition of bacteria served as negative control.

These reactions were stopped by adding cold quenching solution comprising Trypan blue. The samples were washed twice with cold saline solution. Erythrocytes were lysed and cells fixed by adding the lysis reagent included with the assay kit. A DNA stain was subsequently used in order to rule out artifacts caused by bacteria aggregates and thrombocytes.

The samples were analyzed on a FACS Calibur (Becton Dickinson, San Jose, USA) within 60 minutes by means of FACS (fluorescence activated cell sorting), a form of flow cytometry based on fluorescently labeled cells.

Results

The data shown in FIGS. 1 to 6 show mean values as bar heights and standard deviations as error bars.

In FIG. 1, bar charts show the count for erythrocytes (RBC, red blood cells), thrombocytes (PLT, platelets) and leukocytes (WBC, white blood cells) for the leukocyte fraction (left in each case), in the HES supernatant (center in each case) and in the final leukocyte preparation (right in each case). The cell count is shown on a logarithmic scale. It is clear that the erythrocyte count is already reduced by more than 98% in the HES supernatant with respect to the leukocyte fraction and only 0.4% of the original amount is present in the leukocyte preparation. The concentration of the thrombocytes is reduced by only 7% in the HES supernatant, but has fallen away to 6.1% of the original concentration in the leukocyte preparation. The concentration of the leukocytes has fallen away to 49.8% of the concentration originally present in the leukocyte fraction.

Thus, the leukocytes in the leukocyte concentration are concentrated substantially more strongly in comparison with the erythrocytes and the thrombocytes than was the case in the prior art.

FIG. 2 shows the counts for leukocyte types in the leukocyte film pool (leukocyte fraction) after 12 hours, in the HES supernatant after 12 hours and in the final leukocyte preparation or leukocyte concentration after 12 hours, 24 hours, 48 hours and 72 hours, specifically for the leukocyte types of the monocytes (top), lymphocytes (center) and granulocytes (bottom).

It is clear that the decrease in leukocyte concentration in the various method steps affects the various types of leukocytes approximately equally. After preparation of the final leukocyte preparation, the ratios and the counts for the various leukocyte types in the leukocyte preparation no longer substantially change.

The survival rate (vitality) was, as shown in Table 1 below, more than 98% over the entire observation period.

TABLE 1

| Time after blood donation (h) | Viability (%) |
| --- | --- |
| 12 | 99.8 ± 0.3 |
| 24 | 99.7 ± 0.3 |
| 48 | 98.7 ± 0.3 |
| 72 | 98.7 ± 0.3 |

As shown in FIG. 3, the proportion of granulocytes (PMN, polymorphonuclear leukocytes) which carried out phagocytosis with regard to fluorescein-labeled *E. coli* was more than 95% at all time points, i.e. over the entire storage period. This activity was established at body temperature, whereas the activity is greatly reduced at 0° C. The measurements took place using fluorescence cytometry with the assay kit Phagotest®.

FIG. 4 shows the result of the measurement of DHR 123 oxidation occurring during granulocyte respiratory burst in response to the presence of *E. coli* and in their absence, measured in fluorescence cytometry with the assay kit Phagoburst®. The samples admixed with *E. coli* led to the result of the right-hand bars relating to the various storage time points; the negative control admixed with PBS led to the activities as per the left-hand bars. Here, it is clear that more than 95% of the granulocytes of the active sample were active and a base activity increased over the course of storage.

FIG. 5 shows the result of a measurement of oxidative burst of samples from the leukocyte preparation by measuring chemiluminescence with lucigenin, the active sample being admixed with zymosan, the negative sample with PBS. The respiratory burst response remained high in all cases, whereas a slight base activity built up toward the end of the investigation period.

The same emerges as per FIG. 6 for the investigation of chemiluminescence with luminol in the leukocyte preparation, likewise by addition of zymosan in the active sample and with PBS in the passive sample.

Second Exemplary Embodiment

The second exemplary embodiment describes the preparation of the leukocyte preparation from granulocyte apheresis products. The analyses were carried out as per the first exemplary embodiment.

Healthy voluntary donors were stimulated with dexamethasone and G-CSF for a few hours prior to apheresis in accordance with current German transfusion regulations in order to increase the granulocyte yield. Apheresis was carried out on a COBE spectra (Caridian BCT, Garching Germany) in accordance with manufacturer's instructions.

Under sterile conditions, the granulocyte apheresis product was directly mixed with Infukoll® HES 6% (Mw:200 000) in a 1:2 ratio in the donor bag and subsequently hung, with the connection pieces upwards, for the purpose of sedimentation. During the sedimentation phase (about 40 min at 22±2° C.), the blood bag was checked at regular intervals by visual inspection for a clear separating layer between the erythrocyte pellet and leukocyte-containing supernatant. Once a clear separating layer was attained (about 40 minutes), the supernatant, which contained for the most part leukocytes and thrombocytes, was transferred to a new bag using a manual blood press. In order to remove the majority of the remaining thrombocytes, the pressed-out supernatant was washed twice with physiological NaCl solution (0.9%). Following the second wash step, the cleaned-up granulocyte concentrate was resuspended in blood group-identical CPD plasma and stored without movement in a thrombocyte storage bag at 22±2° C.

By means of the method described here, it was possible to achieve a depletion of 98% of the erythrocytes and 95% of the thrombocytes. During cleanup, there was merely a loss of 26% of the leukocytes, and so 74% of the leukocytes were available for storage.

FIGS. 7 to 13 show the results for the leukocyte preparation of the second exemplary embodiment.

Figure 7:
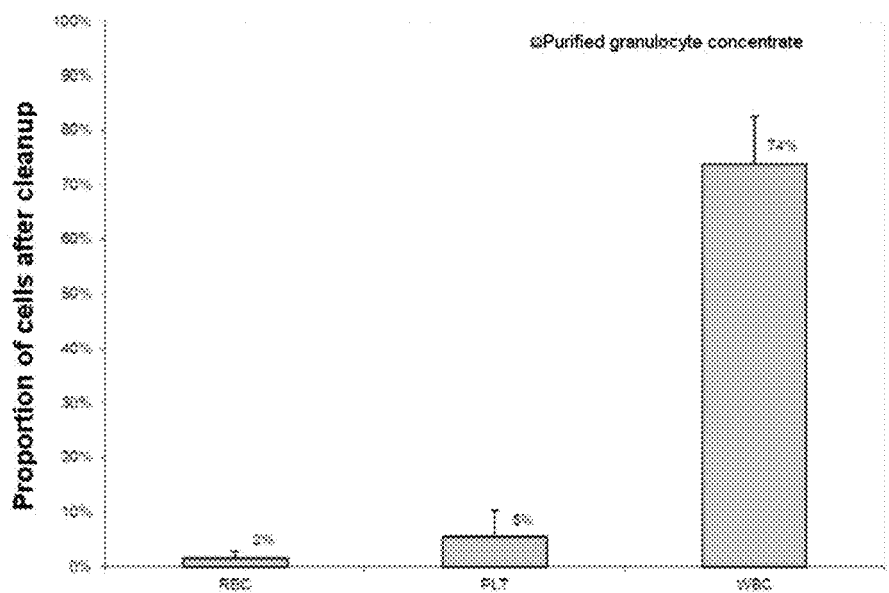

For instance, the depletion of the individual blood components erythrocytes, thrombocytes and leukocytes can be seen in FIG. 7, of which 2%, 5% and 74% remained.

Figure 8:
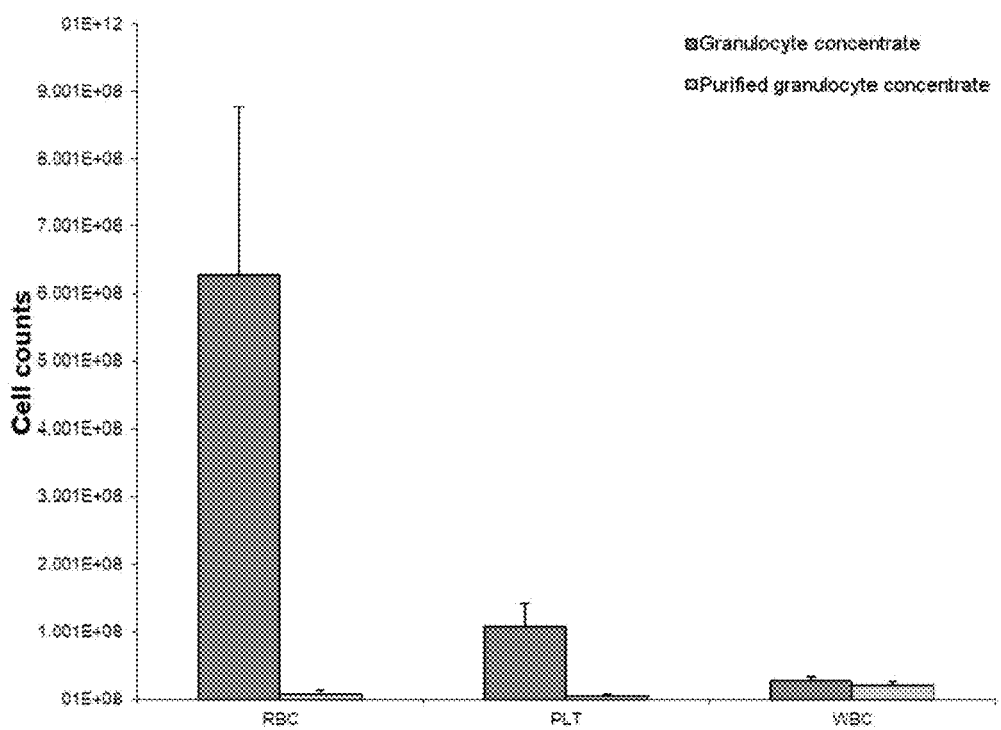

FIG. 8 shows the absolute cell counts for these blood components for the starting preparation, the granulocyte fraction or the granulocyte concentrate, and the granulocyte preparation according to the invention ("purified granulocyte concentrate"), in which the leukocytes now form the majority.

Figure 9:
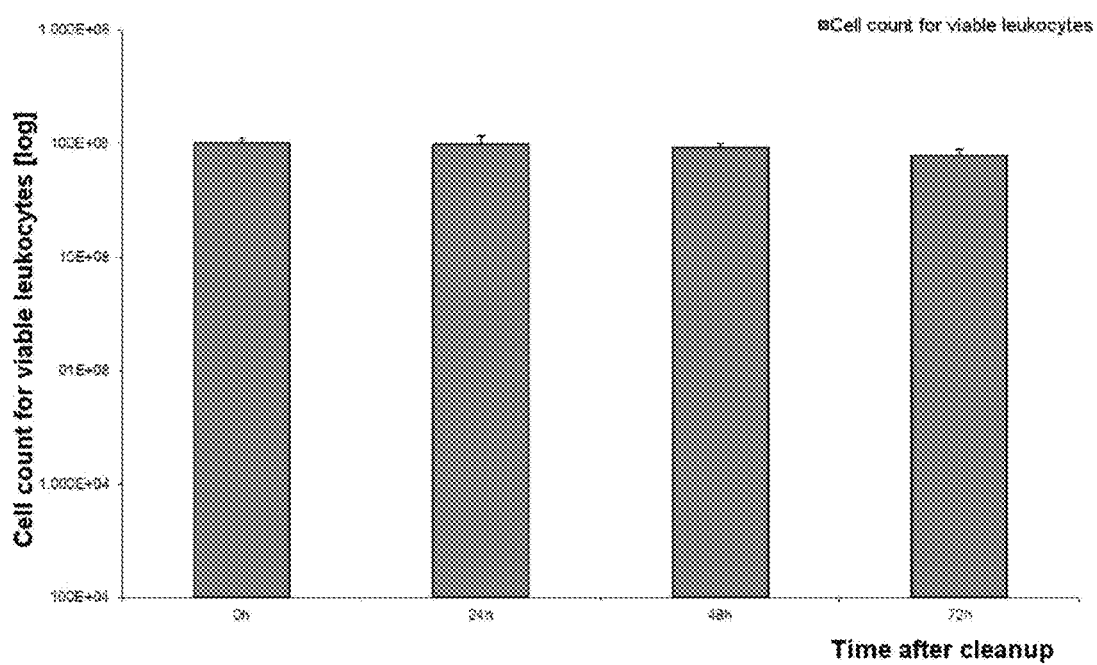

From FIG. 9, it can be seen that the cell count for viable leukocytes in the preparation did not substantially decrease even after 72 hours of storage.

Figure 10:
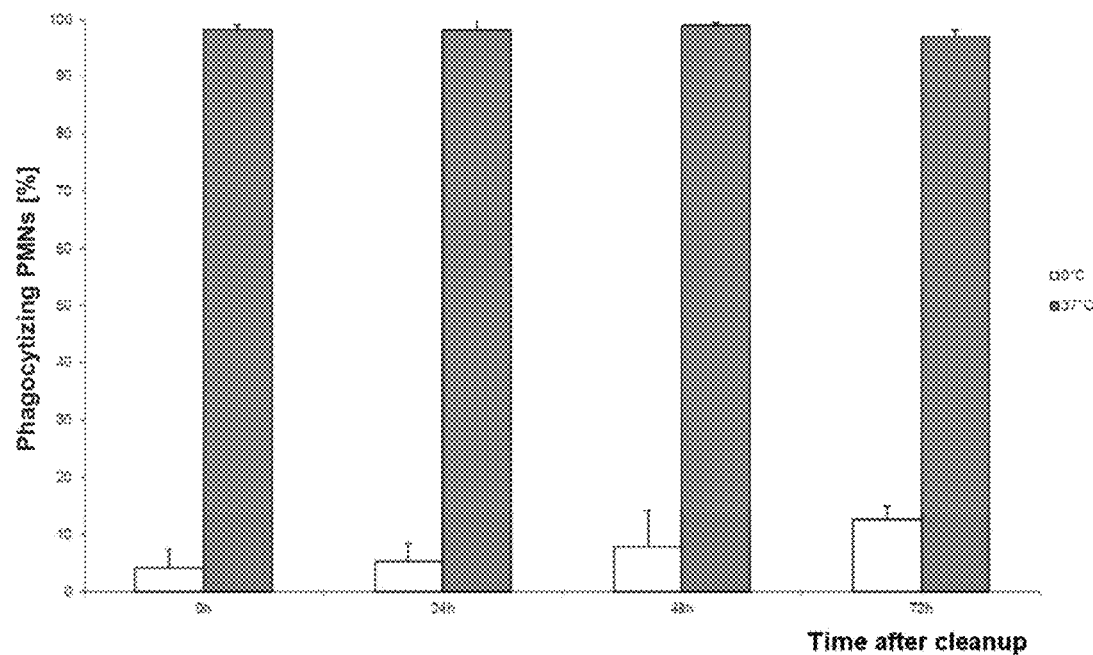
Figure 11:
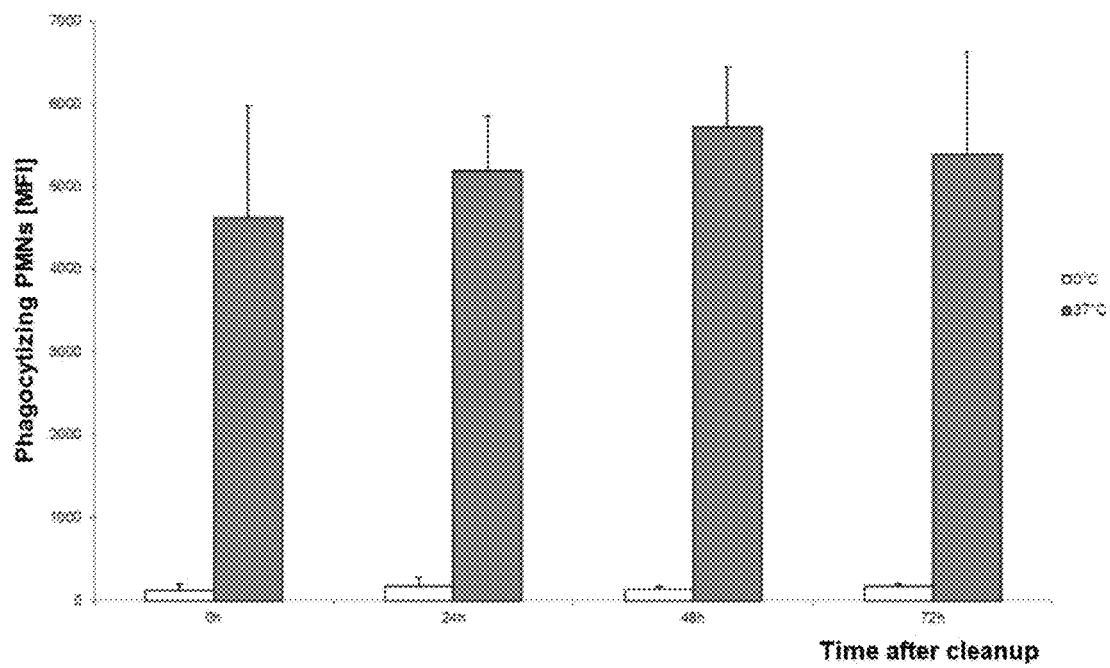

FIG. 10 shows that the relative number of phagocytizing granulocytes remains at almost 100% over the course of storage up to 72 hours after cleanup, whereas the negative sample increases only slightly. In relation to this, FIG. 11 shows the mean fluorescence index (MFI), which indicates how strong the mean fluorescent signal of an individual cell is. This is consistently strong at 37° C.; the negative sample remains inconspicuous.

FIG. 12 shows the relative number of oxidizing granulocytes. This is close to 100% over the entire storage period, with even the granulocytes of the negative sample largely conducting oxidation. FIG. 13 shows the mean fluorescence response (likewise mean fluorescence index, MFI) per cell with regard to FIG. 12, and it is clear from this that the activity of the granulocytes of the active sample is consistently strong, whereas the negative sample, as to be expected, develops only a weak activity.

The method according to the invention and the leukocyte preparation according to the invention eliminate the disadvantages of current granulocyte apheresis products with regard to the lack of purity, the short shelf life and, where applicable, the need for a prestimulation of donors and their stress owing to infusion of some of the citrate and sedimentation accelerator during apheresis. The leukocyte preparation or granulocyte preparation according to the invention is storable for at least 72 hours without substantial loss of function. The granulocyte or leukocyte preparation can be prepared within a short time, about three and a half hours, and with low costs. The method is easy to carry out and can be carried out in a completely closed system, accommodating safety with regard to potential biological, toxicological or chemical impurities. Furthermore, no specific donor is directly required for the preparation process, since the leukocyte films are prepared in large amounts in any blood bank during normal operation. Specific prestimulation of donors with steroids or G-CSF is also not necessary, lowering the potential health risks for donors and also contributing to cost and time savings.

Third Exemplary Embodiment

The third exemplary embodiment describes the preparation of a leukocyte preparation from granulocyte apheresis products. The analyses were carried out as per the first exemplary embodiment.

The granulocyte apheresis products were prepared as per the second exemplary embodiment.

Under sterile conditions, the granulocyte concentrate was directly mixed with HES 6% (hydroxyethyl starch, molecular weight:200 000 daltons) in a 1:0.5 ratio in the donor bag. Subsequently, an empty bag was aseptically welded on using a blood bag/tubing welder (Terumo BCT Europe, Garching, Germany), though the connection weld was not opened, and the donor bag was hung, with the connection tubing upwards, for the purpose of sedimentation. During the sedimentation phase (about 40 min at room temperature), the donor bag was visually checked at regular intervals for a sharp separating layer between the erythrocyte pellet and leukocyte-rich supernatant. Once there was such a separating layer, the weld in the connection tubing between the bags was opened and the leukocyte-containing phase (supernatant) was pressed out into the available empty bag using a manual blood bag press.

In this third exemplary embodiment, two different variants of further processing (washing of the leukocyte sediment with 0.9% NaCl solution) were compared.

In variant 1, after the leukocyte-containing supernatant had been pressed out, a new empty bag was aseptically welded onto the bag containing the leukocyte-containing supernatant (connection weld remained closed) and the supernatant was centrifuged at 300 g at 22±2° C. for 15 minutes with a weak brake. After opening of the connection weld, the supernatant was pressed out using a manual blood press and discarded. In order to remove the majority of the thrombocytes, the leukocyte pellet was washed twice with physiological NaCl solution (0.9%) and centrifuged at 300 g at 22±2° C. for 15 minutes with a weak brake (slowly coming to a standstill over several minutes). Following the second wash step, the cleaned-up granulocyte concentrate was gathered in blood group-identical CPD plasma and analyzed.

Variant 2 of the third exemplary embodiment differs from variant 1 of the third exemplary embodiment in the figures for the centrifugation steps. Thus, the sedimentation supernatant and the leukocyte pellets resuspended in 0.9% NaCl solution were in each case centrifuged at 300 g at 4° C. for 5 minutes with a strong brake (comparatively faster stop within less than one minute).

By means of the two cleanup variants described here, it was possible to achieve a depletion of more than 98% of the erythrocytes. However, the two variants show distinct differences in the depletion of thrombocytes. Thus, in the case of variant 1 (15-minute centrifugation with weak brake), only 70% of the thrombocytes were depleted, whereas in the case of variant 2 (5-minute centrifugation), 95% could be removed. In the case of variant 1, there was only a loss of 27% of the leukocytes during cleanup, and in the case of variant 2, this was 33%.

In FIG. 14, the depletion of the individual blood components leukocytes (WBC, white blood cells), erythrocytes (RBC, red blood cells) and thrombocytes (PLT, platelets) for both variants can be seen, of which 73%, 2% and 30% are retained in the case of variant 1 and 67%, 1% and 5% are retained in the case of variant 2 (mean values from 2 experiments in each case).

Fourth Exemplary Embodiment

The fourth exemplary embodiment describes the preparation of a leukocyte preparation from granulocyte apheresis products in accordance with the variant 2 described in the third exemplary embodiment and the subsequent storage in blood group-identical CPD plasma over a period of 72 hours with buffering of pH.

Following the sedimentation and cleanup of the granulocyte apheresis product, the cell concentration was adjusted to $5 \cdot 10^7$ leukocytes/ml, and so $1 \cdot 10^{10}$ leukocytes in 200 ml of CPD plasma were stored at room temperature in a thrombocyte storage bag without agitation. During this storage, the thrombcyte storage bag rested on grids in order to guarantee full contact of the bag surface with the air. Storage was carried out in two groups, and in the case of one of the storage groups, the pH, once it was less than pH 7.2, was corrected with a corresponding amount of 8.4% sodium bicarbonate solution (NaBic 8.4%) such that it was within the physiological range of human blood (7.35-7.45) again.
Analysis After 0, 24, 48, 72 and 144 hours, the two leukocyte storage groups were mixed well and 3 ml samples were taken in each case under sterile conditions for analysis.

At each time point, the cell concentration and the total cell count for the samples were determined. Furthermore, viability was ascertained using a Trypan blue exclusion assay and functionality in terms of phagocytosis and respiratory burst was investigated using fluorescence cytometry. All the analyses were carried out as described in the first exemplary embodiment.
Results The data shown in FIGS. 15 to 18 are mean values and their standard deviations.

Figure 15:
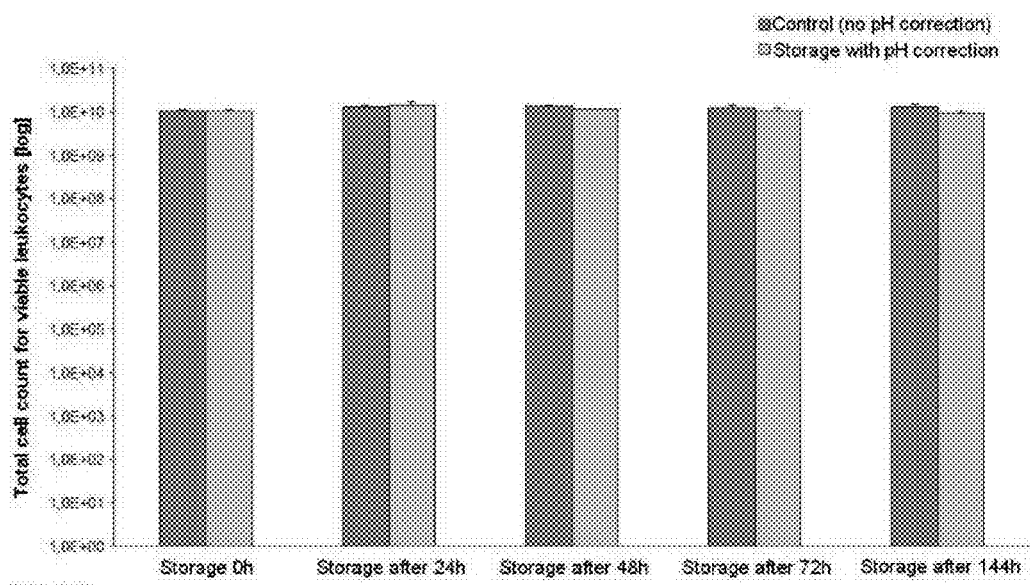

From FIG. 15, it can be seen that the cell counts for viable leukocytes do not substantially decrease over the storage period of 144 hours. In addition, it can be established that pH buffering using 8.4% sodium bicarbonate solution does not have any negative effects on the cell counts.

Figure 16:
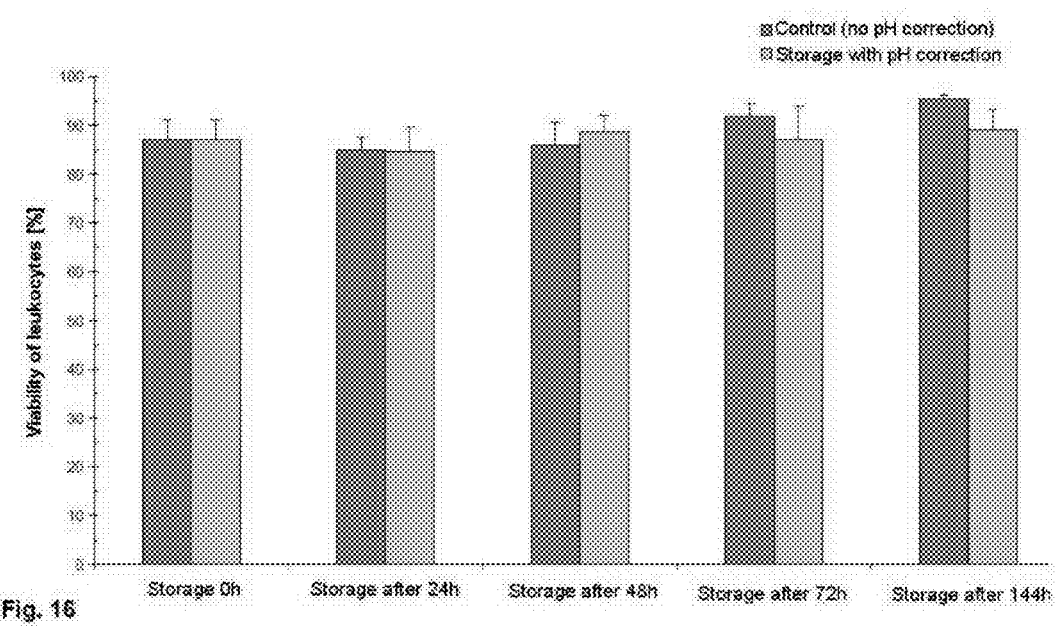

The leukocyte viabilities over the storage period of 144 hours, shown in FIG. 16, also show that there is no negative influence resulting from pH buffering. Even at the end of storage, the viability of the two storage variants is >85%.

Figure 17:
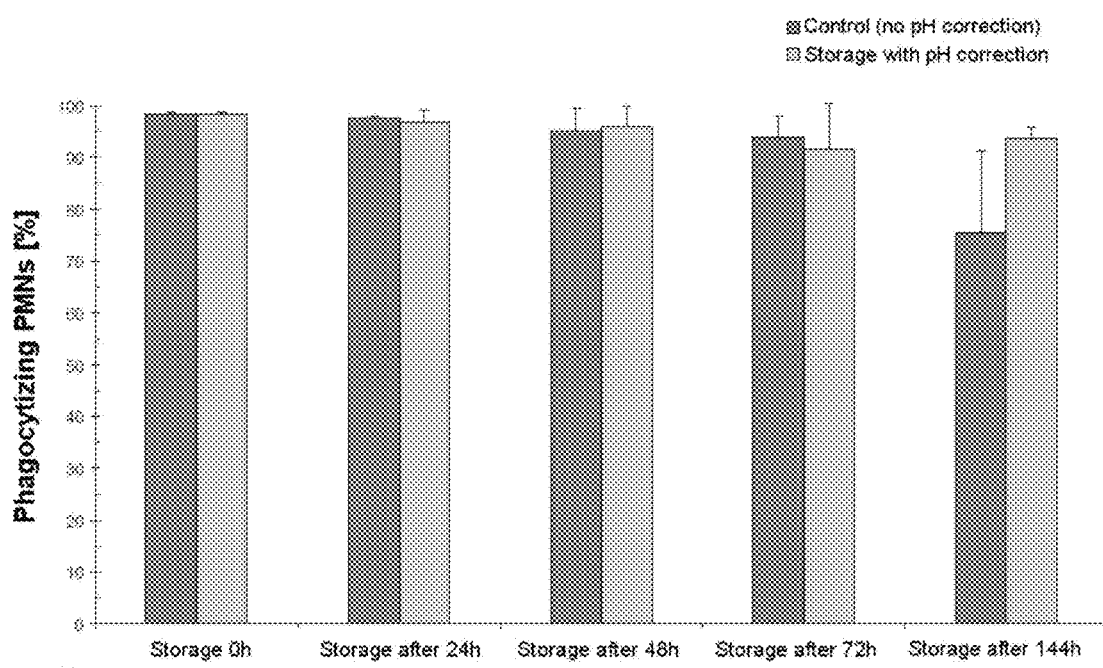

FIG. 17 shows that the relative number of phagocytizing granulocytes (PMN, polymorphonuclear leukocytes) hardly changes up to 72 hours after start of storage in the case of both storage variants and is >90%. However, it can be clearly seen that the relative number of phagocytizing granulocytes stored in a buffered CPD plasma remained constant even after a 144-hour storage period in comparison with the unbuffered control group.

Figure 18:
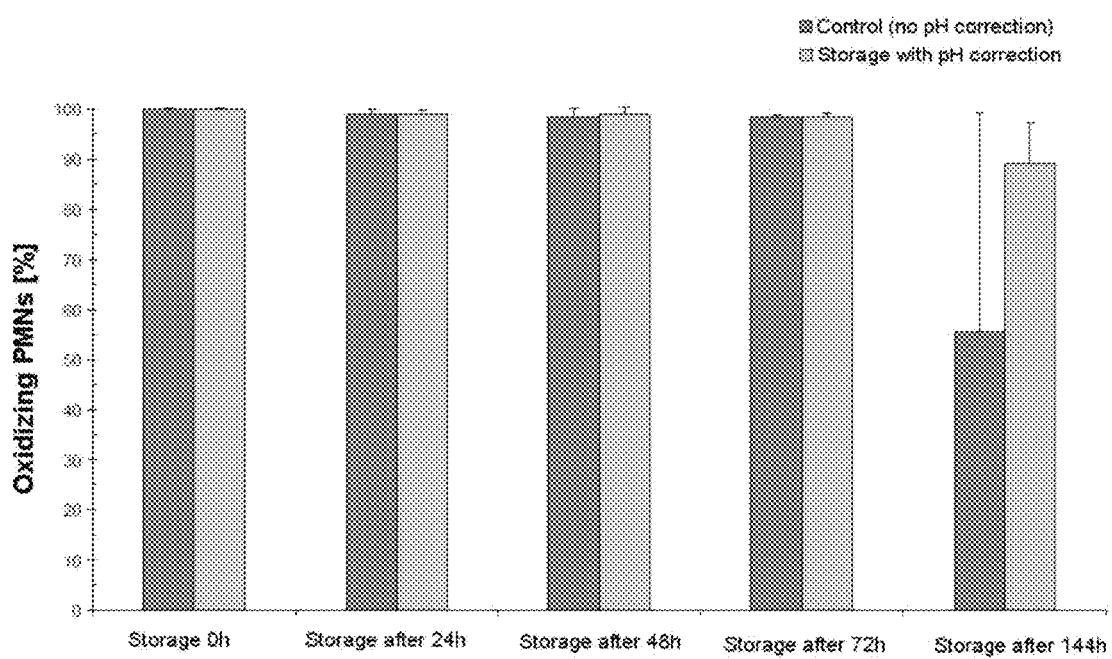

FIG. 18 shows the percentage of granulocytes which produce oxygen radicals (oxidative burst), described in the legend in simplified form as "Oxidizing PMN". This percentage is approximately 100% both in the case of the control group and in the case of storage with pH correction up to 72 hours. Here too, it is possible to see the positive influence of pH correction on the relative number of oxidizing granulocytes after 144 hours, though in the control, a high range of variation can be seen, which may be due in part to donor differences.

The storage variant described in the fourth exemplary embodiment (storage with pH correction) and the results shown showed that storage of granulocytes without substantial impairment of cell count, viability and relative number of phagocytizing and oxidizing cells is possible over a period of 144 hours after cleanup.

Fifth Exemplary Embodiment

The fifth exemplary embodiment describes the preparation of a leukocyte preparation from granulocyte apheresis products in accordance with the variant 2 described in the third exemplary embodiment and the subsequent storage in blood group-identical CPD plasma with the additive solution PAGGS-M over a period of 72 hours.

The additive solution PAGGS-M contains not only sodium chloride, sodium dihydrogen phosphate dihydrate and disodium hydrogen phosphate dihydrate, but also glucose monohydrate, mannitol, adenine and guanosine.

Following the sedimentation and cleanup of the granulocyte apheresis product, the cell concentration of the two storage groups was adjusted to $5 \cdot 10^7$ leukocytes/ml, and so $1 \cdot 10^{10}$ leukocytes in 200 ml of storage medium were stored at room temperature in a thrombocyte storage bag without agitation. One experimental group contained pure blood group-identical CPD plasma (control) as storage medium. The other was admixed with a mixture of CPD plasma with a 35% volume of the additive solution PAGGS-M. The thrombocyte storage bags rested on grids over the entire storage period in order to guarantee full contact of the bag surface with the air. In the case of both storage groups, the pH was corrected with 36.34% TRIS in the event of a pH of less than 7.2 so that it was within the physiological range of human blood (7.35-7.45) again.

Analysis

After 0, 24, 48 and 72 hours, the two leukocyte storage groups were mixed well and 3 ml samples were taken in each case under sterile conditions for analysis.

At each time point, the cell concentration and the total cell count for the samples were determined. Furthermore, viability was ascertained using a Trypan blue exclusion assay and functionality in terms of phagocytosis and respiratory burst was investigated using fluorescence cytometry. All the analyses were carried out as described in detail in the first exemplary embodiment.

Results

The data shown in FIGS. 19 to 24 are mean values and their standard deviations.

Figure 19:
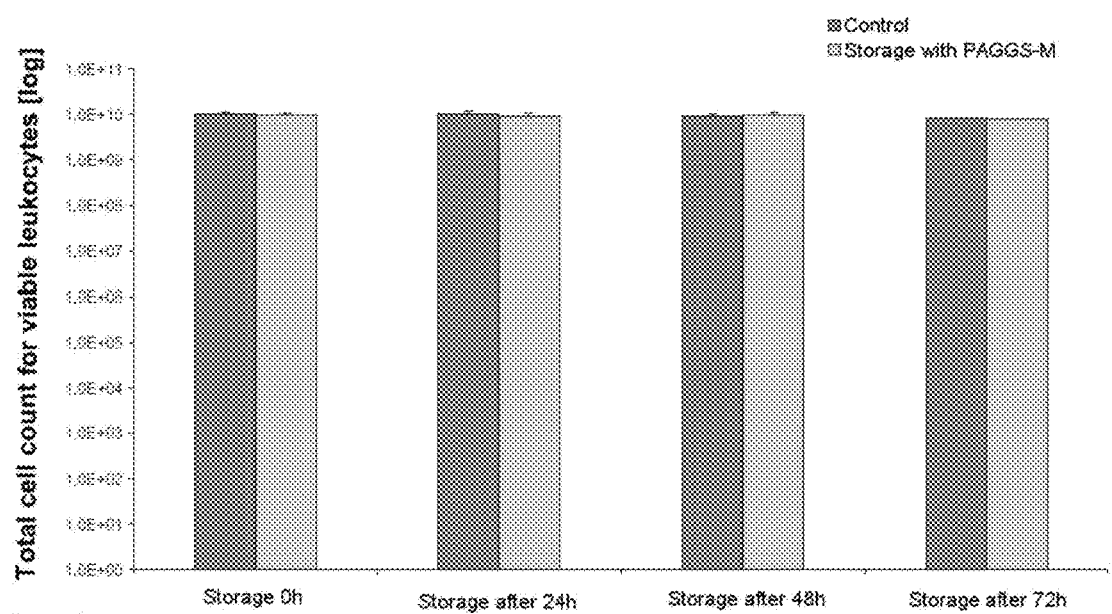
Figure 20:
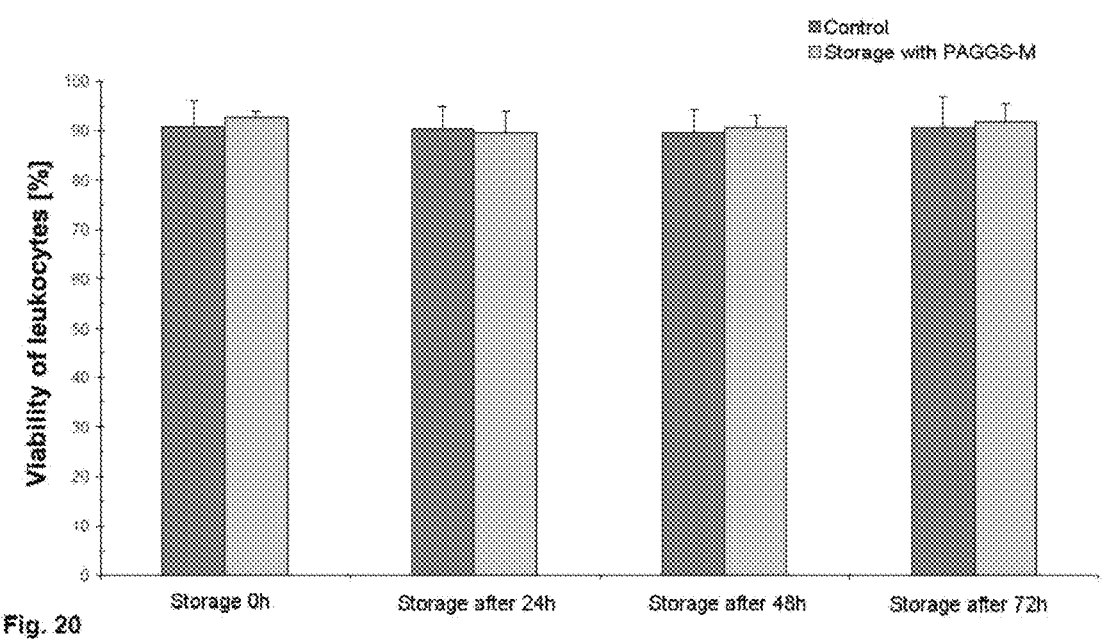

On the basis of FIGS. 19 and 20, it can be established that both the total cell count for viable leukocytes and viability (>90%) remain stable over the storage of 72 hours. Thus, no negative influence owing to the additive solution can be identified.

Figure 21:
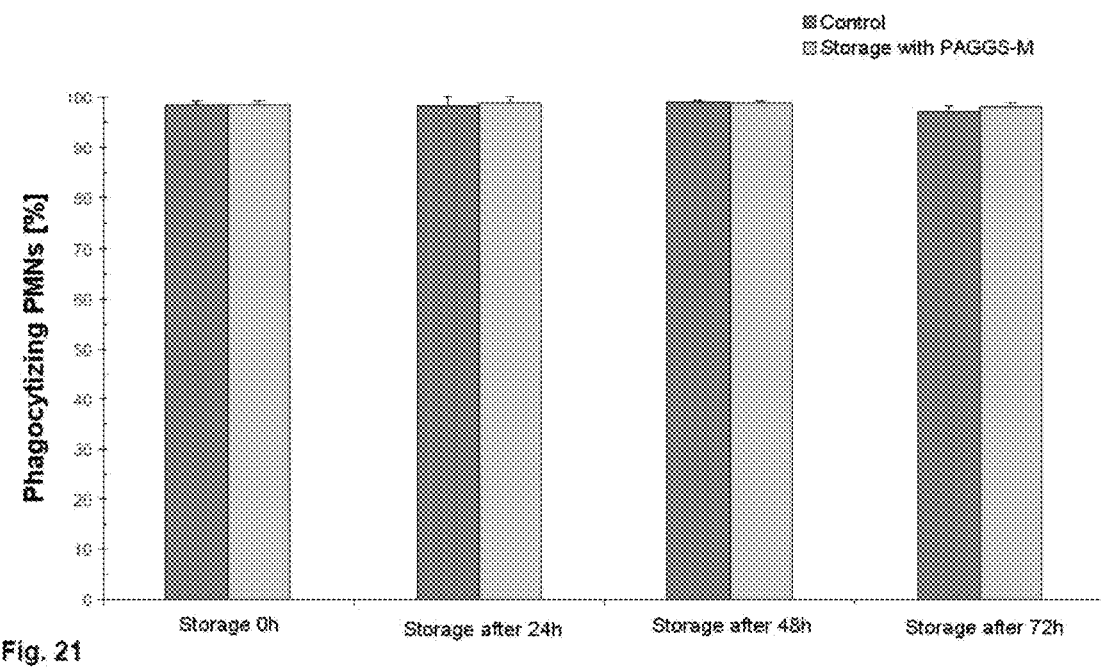
Figure 22:
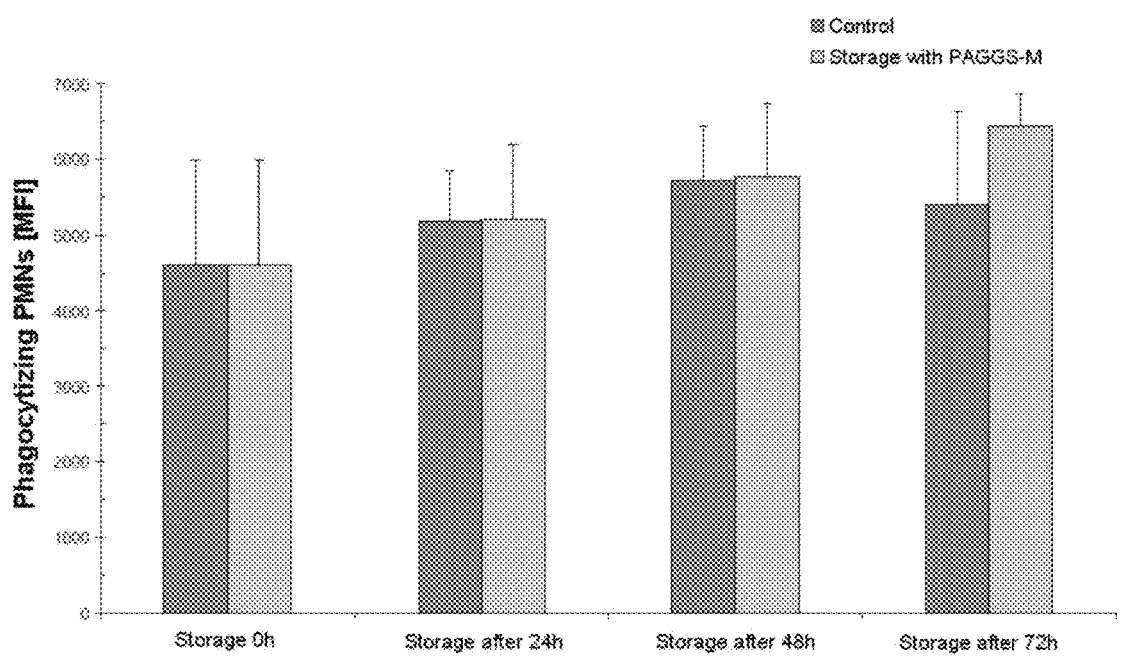

It can be seen from FIG. 21 that the relative number of phagocytizing granulocytes (PMN, polymorphonuclear leukocytes) hardly changes up to 72 hours after start of storage in the case of both storage variants and is almost 100%. FIG. 22 shows the mean fluorescence index (MFI) per individual cell, based on the results from FIG. 21. It is clear from this that the addition of the additive solution PAGGS-M leads to an increase in the phagocytosis capacity per cell over 72 hours, whereas the control group remains consistently strong over the same period.

Figure 23:
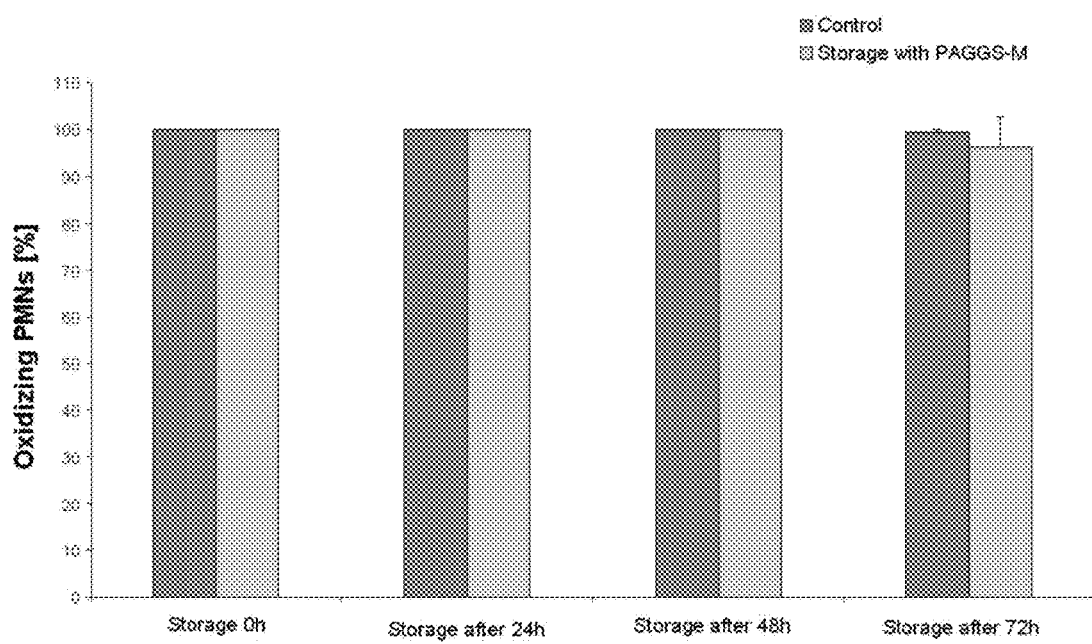
Figure 24:
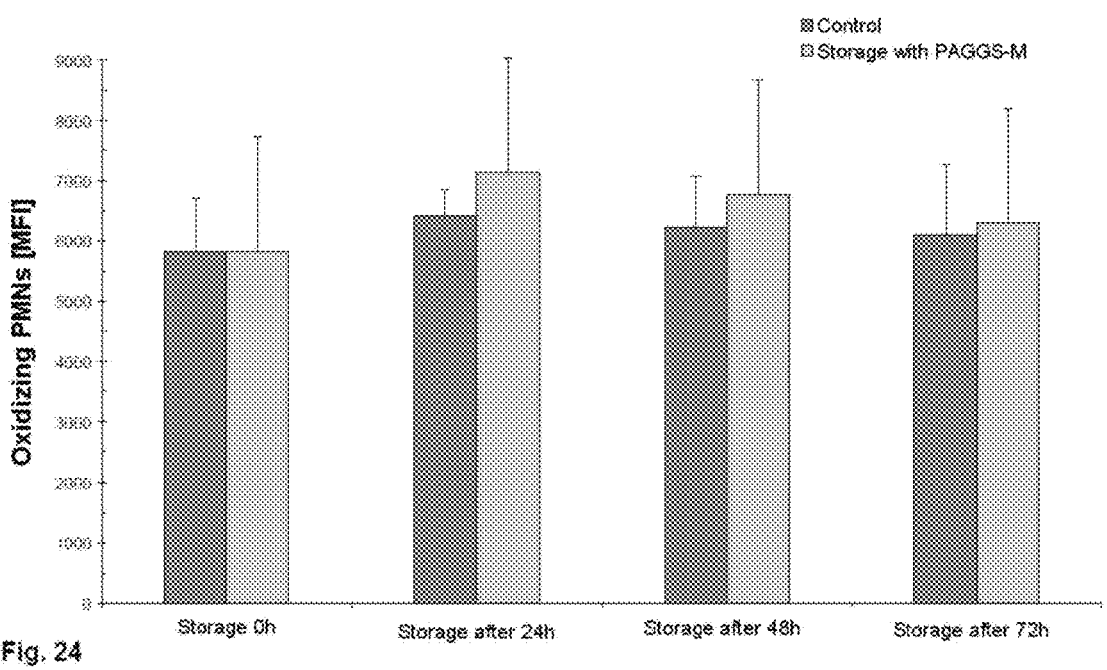

FIG. 23 shows the relative number of oxidizing granulocytes. This is approximately 100% over 72 hours in the case of both storage groups. It can be concluded from the MFI per oxidizing cell, shown in FIG. 24, that the granulocytes remain consistently strong in their activity in the control over the storage period of 72 hours. In the case of storage with additive solution, the activity of the granulocytes is somewhat increased.

By means of the storage method described in the fifth exemplary embodiment (storage with additive solution PAGGS-M), it was possible to show not only that granulocytes can be stored without substantial impairment of cell count, viability, relative number of phagocytizing and oxidizing cells and their capacity over a period of 72 hours after cleanup, but also that the addition of PAGGS-M can improve the performance of the granulocytes.

Sixth Exemplary Embodiment

The sixth exemplary embodiment describes the preparation of a leukocyte preparation from granulocyte apheresis products in accordance with the variant 2 described in the third exemplary embodiment and the subsequent storage in blood group-identical CPD plasma containing 35% PAGGS-M and the immune system-related preparation "Immuno-akut®" from MensSana AG over a period of 120 hours.

The immune system-related preparation "Immuno-akut®" contains not only vitamins B6, B12, C, D and E, but also folic acid, various carotenoids and trace elements.

Following the sedimentation and cleanup of the granulocyte apheresis product, the cell concentration of the two storage groups was adjusted to $5 \cdot 10^7$ leukocytes/ml, and so $1 \cdot 10^{10}$ leukocytes in 200 ml of CPD plasma/PAGGS-M mixture were stored at room temperature (22±2° C.) in a thrombocyte storage bag without agitation. Dissolved and sterile-filtered, approximately 30 mg of the powder of the immune system-related preparation were added to one of the two storage groups. The thrombocyte storage bags rested on grids over the entire storage period in order to guarantee full contact of the bag surface with the air. In the case of both storage groups, the pH (if <7.2) was corrected when required with 36.34% TRIS so that it was within the physiological range of human blood (7.35-7.45) again.

Analysis

After 0, 24, 48, 72, 96 and 120 hours, the two leukocyte storage groups were mixed well and 3 ml samples were taken in each case under sterile conditions for analysis.

At each time point, the cell concentration and the total cell count for the samples were determined. Furthermore, viability was ascertained using a Trypan blue exclusion assay and functionality in terms of phagocytosis and oxidative burst was investigated using fluorescence cytometry. Respiratory burst was additionally measured by means of chemiluminescence measurement using lucigenin. All the analyses were carried out as described in detail in the first exemplary embodiment.

Results

The data shown in FIGS. 25 to 31 are mean values and their standard deviations.

Figure 25:
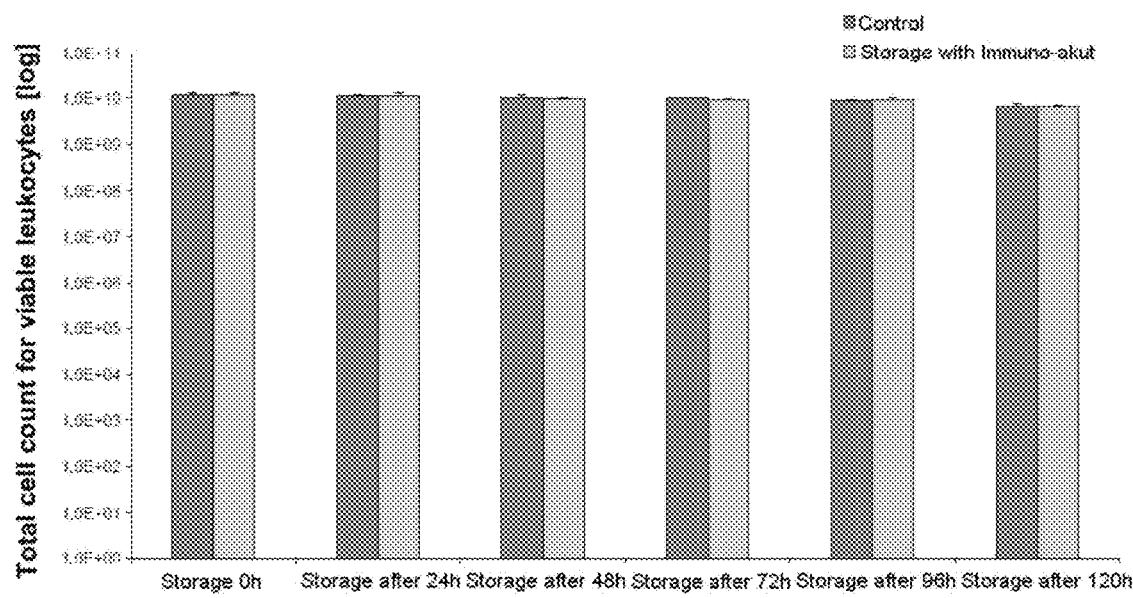
Figure 26:
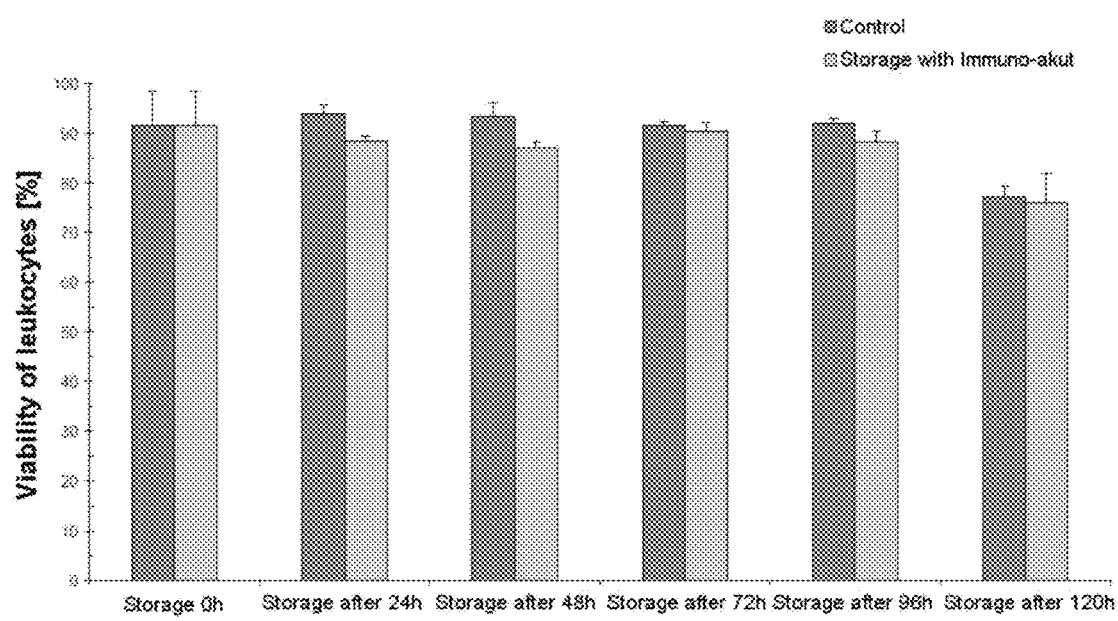

On the basis of FIG. 25, it can be established that the total cell count for viable leukocytes remains stable over the storage period of 120 hours. It is clear from FIG. 26 that viability remains constant over 96 hours in the case of both storage variants, and worsens minimally only after 120 hours. However, no negative influence owing to the Immuno-akut® is apparent over the storage period.

Figure 27:
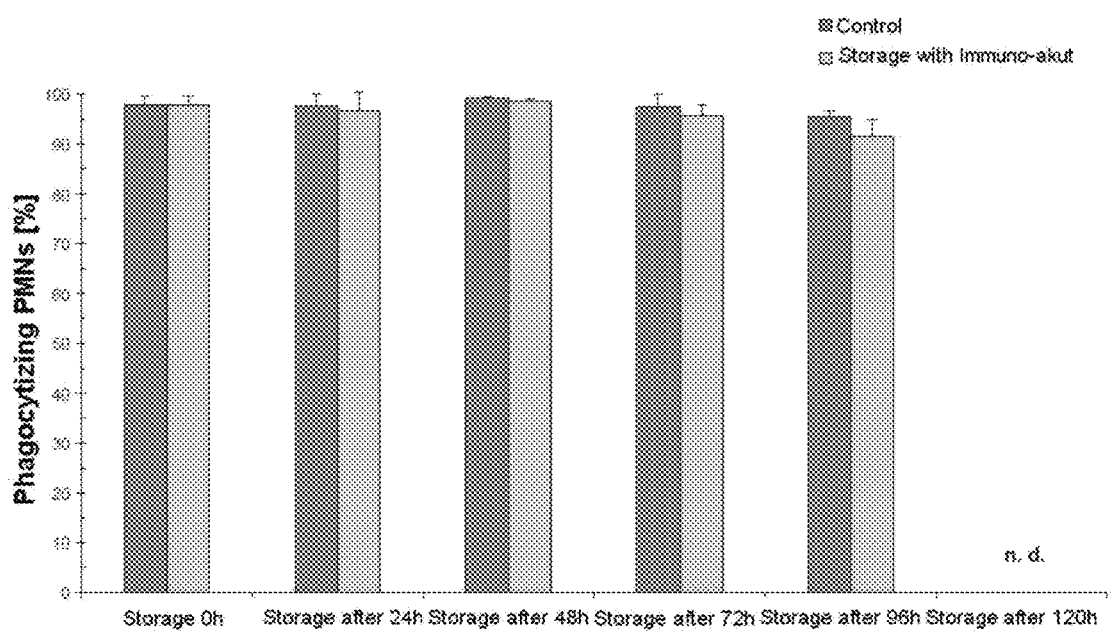
Figure 28:
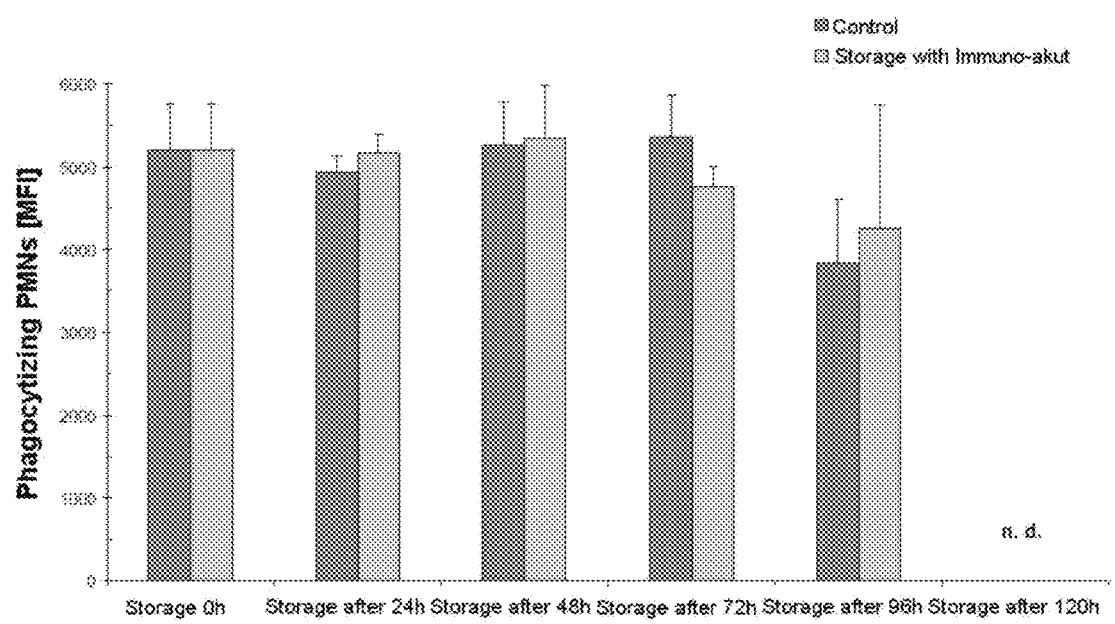

It can be seen from FIG. 27 that the relative number of phagocytizing granulocytes (PMN, polymorphonuclear leukocytes) hardly changes over 96 hours of storage in the case of both storage variants and is almost 100%. FIG. 28 shows the mean fluorescence index (MFI) per individual cell. It is clear that both storage groups have a consistently good phagocytosis capacity over 72 hours. The capacity of the two groups worsens minimally only after 96 hours, it being somewhat lower in the case of storage with the immune system-related preparation.

Figure 29:
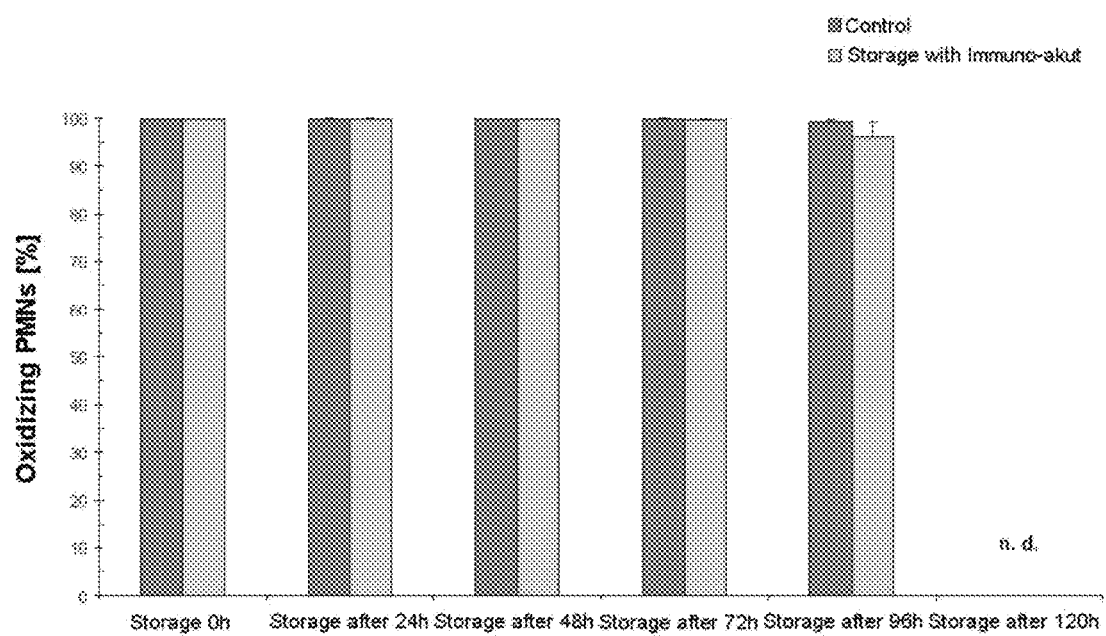
Figure 30:
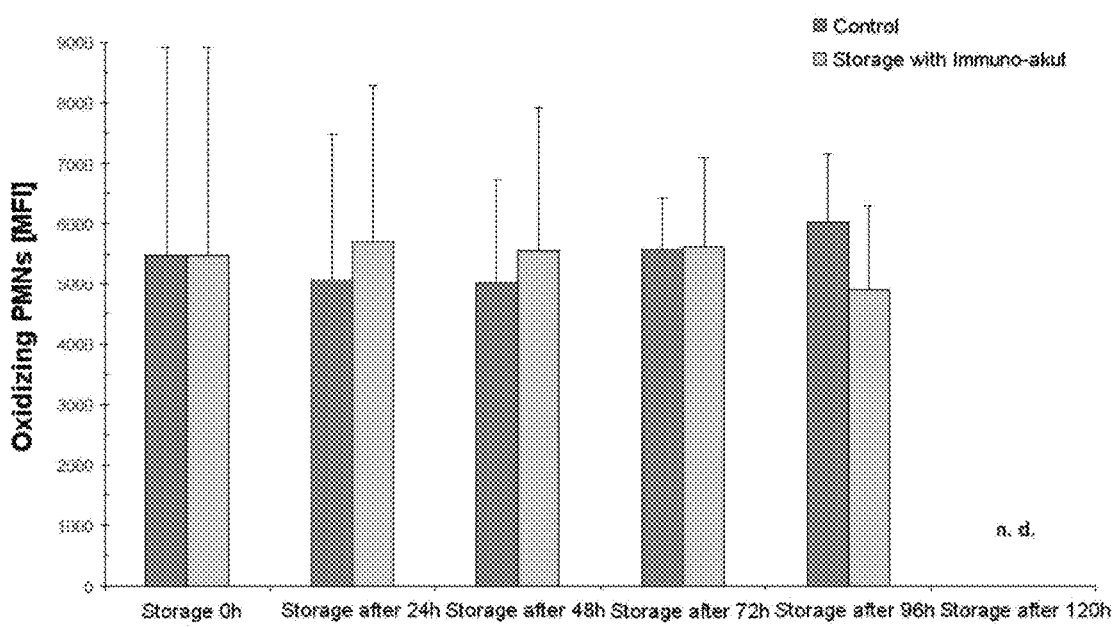

A similar picture is also apparent for the oxidative burst measured using fluorescence flow cytometry. FIG. 29 shows the relative number of oxidizing granulocytes. This is approximately 100% over 96 hours in the case of both storage groups. The MFI per oxidizing cell, shown in FIG. 30, likewise remains consistently good over 96 hours in the case of both storage conditions.

FIG. 31 shows the result of the measurement of respiratory burst in the two storage groups by measurement of chemiluminescence using lucigenin after stimulation of the PMNs with zymosan. Oxidative burst remained consistently high over 72 hours in the case of both storage conditions. After and 120 hours, a minimal worsening of oxyburst becomes apparent.

By means of the storage additive described in the sixth exemplary embodiment (immune system-related preparation "Immuno-akut®"), it was possible to show that granulocytes can be stored without substantial impairment of cell count, viability, relative number of phagocytizing and oxidizing cells and their capacity over a period of 96 hours after cleanup.

Seventh Exemplary Embodiment

The seventh exemplary embodiment describes the partly automated/semiautomated preparation of a leukocyte preparation from a granulocyte apheresis product or a leukocyte film pool. The analyses were carried out as per the first exemplary embodiment.

The individual leukocyte films were pooled as per the first exemplary embodiment. The granulocyte apheresis products were prepared as per the second exemplary embodiment.

Under sterile conditions, the granulocyte concentrate or the leukocyte film pool was directly mixed with HES 6% (MW:200 000) in a 1:0.5 ratio in the donor bag or pool bag. Subsequently, a piece of pump tubing was aseptically connected to the donor/pool bag. The other end of the tubing was likewise aseptically connected to an empty bag (collection bag). The donor or pool bag was hung, with the pump tubing pointing upwards, for the purpose of sedimentation. During the sedimentation phase (30 to 40 minutes at room temperature), the bag was visually inspected at regular intervals for a sharp separating layer between the erythrocyte pellet and leukocyte-rich supernatant. Once there was such a separating layer, the leukocyte-containing supernatant was pumped from the donor or pool bag via the tubing into the collection bag by application of a differential pressure in an upward direction and the donor/pool bag was aseptically welded off. Depending on the volume of the preparation, the flow rate was selected such that the sedimentation time is not substantially influenced (20 to 70 ml/min).

After pumping had been carried out, a further empty bag (waste bag) was aseptically welded onto the collection bag. The collection bag (leukocyte-rich supernatant) and the empty waste bag were centrifuged together at 4° C., 300 g, for 5 minutes. After centrifugation, the collection bag was transferred to a manual blood press and the supernatant was pressed into the waste bag. The waste bag was then aseptically disconnected and discarded. In order to remove the majority of the thrombocytes, the leukocyte pellet in the collection bag was washed twice with physiological NaCl solution (0.9%) and centrifugation at 300 g at 4° C. for 5 minutes. The supernatant was pressed out each time into a waste bag and discarded. Following the second wash step, the cleaned-up granulocyte concentrate or the purified leukocyte film pool was gathered in blood group-identical CPD plasma and analyzed.

By means of the partly automated variant of cleanup of granulocyte apheresis products or leukocyte film pools that is described here, it was likewise possible to attain a depletion of >95% of the erythrocytes and >93% of the thrombocytes in comparison with the granulocyte apheresis product/leukocyte pool. However, this handling leads to a distinctly lower loss of leukocytes. Thus, in comparison to the manual methods and the results thereof described in the first exemplary embodiment or in relation to the variant 2 of the third exemplary embodiment, it was possible to acquire about 20% more of the leukocytes.

FIG. 32 shows the depletion of the individual blood components leukocytes (WBC, white blood cells), erythrocytes (RBC, red blood cells) and thrombocytes (PLT, platelets) for the cleanup of a granulocyte apheresis product. It is thus clear that it was possible to recover, by means of the partly automated cleanup, 89.6% of the leukocytes (manual method: 70% leukocyte content), although the depletion of erythrocytes (96%) and thrombocytes (93%) was equally good in comparison with the manual method.

FIG. 33 shows the depletion results for a leukocyte preparation prepared from a leukocyte film pool. Here too, it was possible to improve the yield of leukocytes (68.6%; manual method: 49.8%) coupled with consistently very good depletion of erythrocytes (96%) and thrombocytes (94%).

Further automation of the wash steps as well (differential pressure or pumping) made it possible to improve the yield of leukocytes even further (figure not shown).

All the stated features, including the features to be learnt on their own from the drawings and also including individual features disclosed in combination with other features, are considered to be essential to the invention on their own and in combination. Embodiments according to the invention can be fulfilled by individual features or a combination of two or more features.

What is claimed is:

1. A method for preparing a leukocyte preparation from a leukocyte fraction, the method comprising:
    a) sedimenting the leukocyte fraction until a dividing line has formed between the sedimented erythrocytes and a leukocyte supernatant, removing the leukocyte supernatant from the sediment, wherein the leukocyte supernatant is collected or remains in a leukocyte container;
    b) sedimenting the leukocytes in the leukocyte container, wherein a low-leukocyte supernatant is formed, and removing the low-leukocyte supernatant from the leukocyte container;
    c) washing the sediment in the leukocyte container with a saline solution, wherein the sedimented cells are resuspended in the saline solution, the solution is sedimented and a resulting supernatant is removed;
    d) resuspending the sediment in the leukocyte container in a storage solution; and
    e) storing the solution from step d) in a gas-permeable bag at a temperature between 20° C. and 25° C. for at least 48 hours.

2. A method according to claim 1 wherein sedimentation is carried out in step a) at an acceleration from 0.5 g to 1000 g.

3. A method according to claim 1, wherein the sedimentation is carried out in step a) with the addition of a sedimentation accelerator.

4. A method according to claim 3, wherein the sedimentation accelerator is selected from the group consisting of hydroxyethyl starch, dextran, Ficoll, Percoll and gelatin.

5. A method according to claim 1, wherein the sedimentation time in step a) is between 5 and 120 minutes.

6. A method according to claim 1, wherein sedimentation of the leukocytes in step b) and/or sedimentation in step c) is carried out by centrifugation.

7. A method according to claim 6 wherein the centrifugation is at an acceleration from 50 to 10000 g.

8. A method according to claim 1, wherein the wash or washes in step c) is repeated one or more times and is processed by one or more of centrifugation, filtration, and filtration with a physiological solution containing 50 to 200 mM sodium chloride.

9. A method according to claim 8, wherein the physiological solution comprises at least one of a second salt and a buffer.

10. A method according to claim 1, wherein the storage solution is selected from at least one of a blood group-identical blood plasma and an aqueous solution containing blood group-identical plasma.

11. A method according to claim 1, wherein the method is carried out aseptically in a closed system.

12. A method according to claim 11, wherein the method is carried out in a system of tubing and bags.

13. A method according to claim 1, wherein before, during or after any of method steps a) to d), at least one additive is added, wherein the at least one additive is selected from the group consisting of pH-stabilizing substances cytokines, growth factors, blood group-identical blood plasma, or albumin, antioxidants, ascorbic acid, glutathione, cysteine, and methionine.

14. A method according to claim 1, wherein before, during or after any of steps a) to e), multiple preparations are pooled.

15. A method according to claim 1, wherein before or after at least one of steps a) to e) or immediately before use, an irradiation takes place.

16. A method according to claim 1, wherein a portion is transferred from one bag to another by at least one of a pressure difference generated manually, a pressure difference generated by a machine, and gravity.

17. A method according to claim 1, wherein the solution in step e) is stored between at least 48 hours and no more than 72 hours.

* * * * *